(12) United States Patent
Lee et al.

(10) Patent No.: US 10,481,154 B2
(45) Date of Patent: Nov. 19, 2019

(54) BIOMARKER DETECTION AND SELF-SEPARATION OF SERUM DURING CAPILLARY FLOW

(71) Applicant: New Jersey Institute of Technology, Newark, NJ (US)

(72) Inventors: Eon Soo Lee, Tenafly, NJ (US); Bharath Babu Nunna, Randolph, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 15/811,186

(22) Filed: Nov. 13, 2017

(65) Prior Publication Data
US 2018/0128823 A1 May 10, 2018

Related U.S. Application Data

(60) Provisional application No. 62/420,178, filed on Nov. 10, 2016, provisional application No. 62/420,195, (Continued)

(51) Int. Cl.
*G01N 33/543* (2006.01)
*B01L 3/00* (2006.01)
(Continued)

(52) U.S. Cl.
CPC .. *G01N 33/54373* (2013.01); *B01L 3/502715* (2013.01); *B01L 3/502753* (2013.01);
(Continued)

(58) Field of Classification Search
CPC ......... G01N 33/54373; G01N 33/5438; G01N 27/227; G01N 27/226; G01N 33/545;
(Continued)

(56) References Cited

U.S. PATENT DOCUMENTS

| 5,958,791 A * | 9/1999 | Roberts | C12Q 1/6816 |
| | | | 204/288 |
| 2006/0160134 A1* | 7/2006 | Melker | G01N 33/53 |
| | | | 435/7.1 |

(Continued)

OTHER PUBLICATIONS

Alcantar, Norma A., et al., "Polyethylene glycol-coated biocompatible surfaces," Journal of biomedical materials research, vol. 51, No. 3, Sep. 2000, pp. 343-351.

(Continued)

*Primary Examiner* — Melanie Brown
(74) *Attorney, Agent, or Firm* — Lerner, David, Littenberg, Krumholz & Mentlik, LLP

(57) ABSTRACT

Molecularly Imprinted Polymers (MIPs) are utilized to detect diseases and minimize false negative/positive scenarios. MIPs are implemented on a nano-electric circuit in a biochip where interactions of MIPs and an Antigen/Antibody (AG/AB) are detected, and disease specific biomarkers diagnosed. Biomarker detection is achieved with interdigitated gold electrodes in a biochip's microchannel. Capacitance changes due to biomarker interaction with AG/AB electrode coating diagnose diseases in a microfluidic environment. Biofluid passes through the microchannel and exposed to the nanocircuit to generate a capacitance difference and diagnose any specific disease in the biofluid sample. Blood capillary flow in a microchannel curved section experience centrifugal forces that separate liquid from solid. Various blood densities and segments experience different centrifugal effects while flowing through the curved section so serum is separated from various solid matter without using external devices.

18 Claims, 28 Drawing Sheets

Related U.S. Application Data filed on Nov. 10, 2016, provisional application No. 62/420,226, filed on Nov. 10, 2016.

(51) Int. Cl.
  *G01N 33/574* (2006.01)
  *G01N 27/22* (2006.01)
  *G01N 33/545* (2006.01)

(52) U.S. Cl.
  CPC ......... *G01N 27/226* (2013.01); *G01N 27/227* (2013.01); *G01N 33/545* (2013.01); *G01N 33/5438* (2013.01); *G01N 33/574* (2013.01); *B01L 3/502746* (2013.01); *B01L 2200/12* (2013.01); *B01L 2200/143* (2013.01); *B01L 2300/0636* (2013.01); *B01L 2300/0645* (2013.01); *B01L 2300/0819* (2013.01); *B01L 2300/0896* (2013.01); *B01L 2300/16* (2013.01); *B01L 2400/0406* (2013.01); *B01L 2400/0409* (2013.01); *G01N 2600/00* (2013.01)

(58) Field of Classification Search
  CPC ............. G01N 33/574; B01L 3/502753; B01L 3/502715; B01L 3/502746
  See application file for complete search history.

(56) References Cited

U.S. PATENT DOCUMENTS

| | | | | |
|---|---|---|---|---|
| 2012/0045838 | A1* | 2/2012 | Krozer | B01J 20/26 436/34 |
| 2012/0156688 | A1* | 6/2012 | McAlpine | B82Y 15/00 435/7.1 |
| 2015/0241374 | A1* | 8/2015 | Belbruno | G01N 33/0047 436/501 |
| 2017/0227486 | A1* | 8/2017 | Bhansali | G01N 27/3278 |

OTHER PUBLICATIONS

Carrara S., et al., "Label-free cancer markers detection by capacitance Biochip", Sensors and Actuators B: Chemical, vol. 136, No. 1, Feb. 2009, pp. 163-172.
Chen L., et al., "Molecular imprinting: perspectives and applications," Chem. Soc. Rev., vol. 45, No. 8, Apr. 2016, pp. 2137-2211.
Chen L., et al., "Recent advances in molecular imprinting technology: current status, challenges and highlighted applications," Chem. Soc. Rev., vol. 40, No. 5, May 2011, pp. 2922-2942.
Cui, Haochen, "Alternating Current Electrokinetics based capacitive affinity biosensor: A point of care diagnostic platform." PhD Diss., University of Tennessee, http://trace.tennessee.edu/utk_graddiss/3411/ Aug. 2015, (141 pages).
Dick J. E., et al., "Enzymatically enhanced collisions on ultramicroelectrodes for specific and rapid detection of individual viruses," Proc. Natl. Acad. Sci., vol. 113, No. 23, Jun. 2016, pp. 6403-6408.
Dreaden, E.C., et al., "The golden age: gold nanoparticles for biomedicine", Chemical Society Reviews, vol. 41, No. 7, Apr. 2012, pp. 2740-2779.
Eddington, David T., et al., "Thermal aging and reduced hydrophobic recovery of polydimethylsiloxane," Sensors and Actuators B: Chemical, vol. 114, No. 1, Mar. 2006, pp. 170-172.
Gerwen, P.V., et al., "Nanoscaled interdigitated electrode arrays for biochemical sensors", Sensors and Actuators B: Chemical, vol. 49, No. 1-2, Jun. 1998, pp. 73-80.
Ginn, Brent T., et al., "Polymer surface modification using microwave-oven-generated plasma," Langmuir 19, No. 19, Sep. 2003, pp. 8117-8118.
Hrncir, E., et al., "Surface tension of blood," Physiological research/Academia Scientiarum Bohemoslovaca, vol. 46.4, Jan. 1997, pp. 319-321.
Jazayeri, Mir Hadi, et al., "Various Methods of Gold Nanoparticles(GNPs) Conjugation to Antibodies," Sensing and Bio-Sensing Research, vol. 9, Jul. 2016, pp. 17-22.
Jencks W. P., "On the attribution and additivity of binding energies," Proc. Natl. Acad. Sci., vol. 78, No. 7, Jul. 1981, pp. 4046-4050.
Laczka, O., et al., "Pathogen detection: A perspective of traditional methods and biosensors", Biosensors and Bioelectronics, vol. 22, No. 7, Feb. 2007, pp. 1205-1217.
Mirsky, V.M., et al., "Capacitive monitoring of protein immobilization and antigen-antibody reactions on monomolecular alkylthiol films on gold electrodes", Biosensors and Bioelectronics, vol. 2. No. 9-10, Nov. 1997, pp. 977-989.
Nunna, B.B., et al., "Ovarian Cancer Diagnosis using Micro Biochip", NIH-IEEE, Strategic Conference on Healthcare Innovations and Point-of-Care Technologies for Precision Medicine, (PCHT15-0056), Nov. 9-10, 2015, Bethesda, MD.
Page M. I., et al., "Entropic contributions to rate accelerations in enzymic and intramolecular reactions and the chelate effect," Proc. Natl. Acad. Sci., vol. 68, No. 8, Aug. 1971, pp. 1678-1683.
Pérez-Moral N., et al., "Comparative study of imprinted polymer particles prepared by different polymerisation methods," Analitica Chimica Acta, vol. 504, No. 1, Feb. 2004, pp. 15-21.
Qureshi, A., et al., "Label-free capacitive biosensor for sensitive detection of multiple biomarkers using gold interdigitated capacitor arrays", Biosensors and Bioelectronics, vol. 25, No. 10, Jun. 2010, pp. 2318-2323.
Qureshi, Anjum, et al., "Label-Free Capacitive Biosensor for Sensitive Detection of Multiple Biomarkers Using Gold Interdigitated Capacitor Arrays," Biosensors and Bioelectronics, vol. 25, No. 10, Jun. 2010, pp. 2318-2323; doi:10.1016/j.bios.2010.03.018.
Thompson, M., et al., "A review of interference effects and their correction in chemical analysis with special reference to uncertainty", Accreditation and Quality Assurance, vol. 10, No. 3, Feb. 2005, pp. 82-97.
Tosar, J.P., et al., "Electrochemical DNA hybridization sensors applied to real and complex biological samples", Biosensors and Bioelectronics, vol. 26, No. 4, Dec. 2010, pp. 1205-1217.
Viswanathan S., et al., "Molecular imprinted nanoelectrodes for ultra sensitive detection of ovarian cancer marker," Biosensors and Bioelectronics, vol. 33, No. 1, Mar. 2012, pp. 179-183.
Wang J., et al., "Field-effect amperometric immuno-detection of protein biomarker," Biosensors and Bioelectronics, vol. 29, No. 1, Nov. 2011, pp. 210-214.
Washburn, E. W., "The dynamics of capillary flow," The Physical Review, vol. XVII, No. 3, Mar. 1921, pp. 273-283.
Wu L., et al., "An amperometric immunosensor for separation-free immunoassay of CA125 based on its covalent immobilization coupled with thionine on carbon nanofiber," Journal of Immunological Methods, vol. 322, No. 1-2, Apr. 2007, pp. 12-19.
Zou, Zhiwei, et al.,"Functionalized Nano Interdigitated Electrodes Arrays on Polymer with Integrated Microfluidics for Direct Bio-Affinity Sensing Using Impedimetric Measurement," Sensors and Actuators A: Physical, vol. 136. No. 2, May 2007, pp. 518-526. doi:10.1016/j.sna.2006.12.006.
Kallempudi SS, Gurbuz Y. A nanostructured-nickel based interdigitated capacitive transducer for biosensor applications. Sensors and Actuators B: Chemical. Dec. 15, 2011;160(1):891-8.
Laczka O, Baldrich E, Munoz FX, del Campo FJ. Detection of *Escherichia coli* and *Salmonella typhimurium* using interdigitated microelectrode capacitive immunosensors: the importance of transducer geometry. Analytical chemistry. Sep. 5, 2008;80(19):7239-47.
Berggren C, Bjarnason B, Johansson G. Capacitive biosensors. Electroanalysis: An International Journal Devoted to Fundamental and Practical Aspects of Electroanalysis. Mar. 2001;13(3):173-80.
Yi M, Jeong KH, Lee LP. Theoretical and experimental study towards a nanogap dielectric biosensor. Biosensors and Bioelectronics. Jan. 15, 2005;20(7):1320-6.
Tsouti V, Boutopoulos C, Zergioti I, Chatzandroulis S. Capacitive microsystems for biological sensing. Biosensors and Bioelectronics. Sep. 15, 2011;27(1):1-11.

(56) References Cited

OTHER PUBLICATIONS

Carlen ET, Weinberg MS, Zapata AM, Borenstein JT. A micromachined surface stress sensor with electronic readout. Review of scientific instruments. Jan. 2008;79(1):015106.

Carlen ET, Weinberg MS, Dubé CE, Zapata AM, Borenstein JT. Micromachined silicon plates for sensing molecular interactions. Applied physics letters. Oct. 23, 2006;89(17):173123.

Park KK, Lee HJ, Yaralioglu GG, Ergun AS, Oralkan Ö, Kupnik M, Quate CF, Khuri-Yakub BT, Braun T, Ramseyer JP, Lang HP. Capacitive micromachined ultrasonic transducers for chemical detection in nitrogen. Applied Physics Letters. Aug. 27, 2007;91(9):094102.

Xiao D, Zhang H, Wirth M. Chemical modification of the surface of poly (dimethylsiloxane) by atom-transfer radical polymerization of acrylamide. Langmuir. Dec. 10, 2002;18(25):9971-6.

Thakor AS, Jokerst J, Zavaleta C, Massoud TF, Gambhir SS. Gold nanoparticles: a revival in precious metal administration to patients. Nano letters. Sep. 7, 2011;11(10):4029-36.

Zhu X, Ahn CH. Electrochemical determination of reversible redox species at interdigitated array micro/nanoelectrodes using charge injection method. IEEE transactions on nanobioscience. Jun. 2005;4(2):164-9.

ASME 2016: HT/FE/ICNMM—Heat Transfer, Fluids Engineering, & Nanochannels, Microchannels, and Minichannels Conferences Conference Program, Jul. 10-14, 2016, pp. 1-130.

Choi Y, Yau ST. Field-effect enzymatic amplifying detector with picomolar detection limit. Analytical chemistry. Jul. 21, 2009;81(16):7123-6.

Tan SH, Nguyen NT, Chua YC, Kang TG. Oxygen plasma treatment for reducing hydrophobicity of a sealed polydimethylsiloxane microchannel. Biomicrofluidics. Sep. 2010;4(3):032204.

Mahony JO, Nolan K, Smyth MR, Mizaikoff B. Molecularly imprinted polymers—potential and challenges in analytical chemistry. Analytica Chimica Acta. Apr. 4, 2005;534(1):31-9.

Wackerlig J, Schirhagl R. Applications of molecularly imprinted polymer nanoparticles and their advances toward industrial use: a review. Analytical chemistry. Nov. 12, 2015;88(1):250-61.

Williams DH, Cox JP, Doig AJ, Gardner M, Gerhard U, Kaye PT, Lal AR, Nicholls IA, Salter CJ, Mitchell RC. Toward the semiquantitative estimation of binding constants. Guides for peptide-peptide binding in aqueous solution. Journal of the American Chemical Society. Aug. 1991;113(18):7020-30.

Nishino H, Huang CS, Shea KJ. Selective protein capture by epitope imprinting. Angewandte Chemie. Int. Ed. Apr. 3, 2006;45:2392-6.

Ertürk G, Hedström M, Tümer MA, Denizli A, Mattiasson B. Real-time prostate-specific antigen detection with prostate-specific antigen imprinted capacitive biosensors. Analytica chimica acta. Sep. 3, 2015;891:120-9.

Severin, Kay, Review: "Molecularly Imprinted Polymers, edited by Borje Sellergren," Angew Chem, Int. Ed. Jul. 2002, 41, No. 6, p. 1071.

Gohagan JK, Prorok PC, Hayes RB, Kramer BS. The Prostate, Lung, Colorectal and Ovarian (PLCO) cancer screening trial of the National Cancer Institute: history, organization, and status. Controlled clinical trials. Dec. 1, 2000;21(6)251S-72S.

Iskierko Z, Sharma PS, Bartold K, Pietrzyk-Le A, Noworyta K, Kutner W. Molecularly imprinted polymers for separating and sensing of macromolecular compounds and microorganisms. Biotechnology advances. Jan. 1, 2016;34(1):30-46.

Whitcombe M_, Martin L, Vulfson EN. Predicting the selectivity of imprinted polymers. Chromatographia. Apr. 1, 1998;47(7-8):457-64.

Mattiasson B, Hedström M. Capacitive biosensors for ultra-sensitive assays. TrAC Trends in Analytical Chemistry. May 1, 2016;79:233-8.

Dou YH, Bao N, Xu JJ, Chen HY. A dynamically modified microfluidic poly (dimethylsiloxane) chip with electrochemical detection for biological analysis. Electrophoresis. Oct. 2002;23(20):3558-66.

Dechtrirat D, Jetzschmann KJ, Stöcklein WF, Scheller FW, Gajovic-Eichelmann N. Protein rebinding to a surface-confined imprint. Advanced Functional Materials. Dec. 19, 2012;22(24):5231-7.

Tai DF, Lin CY, Wu TZ, Chen LK. Recognition of dengue virus protein using epitope-mediated molecularly imprinted film. Analytical Chemistry. Aug. 15, 2005;77(16):5140-3.

Gul O, Heves E, Kaynak M, Basaga H, Gurbuz Y. Label-free, capacitive immunosensor for protein detection. InSensors, 2006. 5th IEEE Conference on Oct. 22, 2006 (pp. 600-603). IEEE.

NIH-IEEE 2015 Strategic Conference on Healthcare Innovations and Point-of-Care Technologies for Precision Medicine, Nov. 9-10, 2015; Technical Program for Monday, Nov. 9, 2015, pp. 1-8.

Altintas Z, Kallempudi SS, Gurbuz Y. Gold nanoparticle modified capacitive sensor platform for multiple marker detection. Talanta. Jan. 15, 2014;118:270-6.

Hoffmann B, Gadau M, Pacschke M, Hintsche R. Conductivity measurements with miniaturised thin film metal electrodes. InSolid-State Sensors and Actuators, 1995 and Eurosensors IX.. Transducers' 95. The 8th International Conference on Jun. 25, 1995 (vol. 2, pp. 837-840). IEEE.

American Cancer Society. Cancer Facts & Figures 2016. Atlanta: American Cancer Society; 2016.

Teeparuksapun K, Hedstrom M, Wong EY, Tang S, Hewlett IK, Mattiasson B. Ultrasensitive detection of HIV-1 p24 antigen using nanofunctionalized surfaces in a capacitive immunosensor. Analytical chemistry. Sep. 28, 2010;82(20):8406-11.

* cited by examiner

Si wafer with
Micro channels

Fabrication of
PDMS Slab

PDMS slab

Punching the inlet
and outlet ports

Binding to plain
(another)PDMS slab

Inlet    Outlet

Contact angle Variation:

Microscopic image of microchannel (200um width) coated with dynabeads-M270 Epoxy (coated with Cancer specific antibodies)

Step 1 – Preparation of the Master Template

Step 2 – Electrode Surface Preparation

Step 3 – Setting up the Ab-MIP (artificial) sensor.
- MIP requires a functional <u>monomer</u> & <u>cross-linker</u> solution and a initiator.
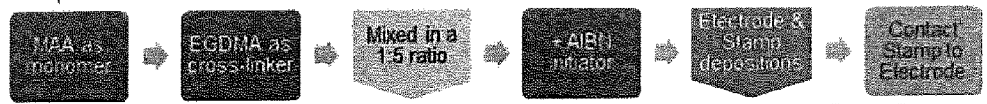
- To initialize the polymerization, UV light was applied for 15 min (365 nm, 400 W)
- Immersion of electrode in 1-dodecanethoil reduces redox currents in the measurement apparatus. This is extremely useful in lowering your noise floor.
Figure-33

Fig. 34

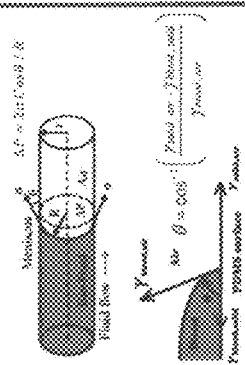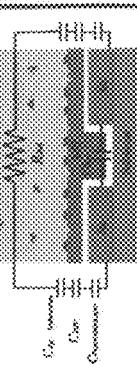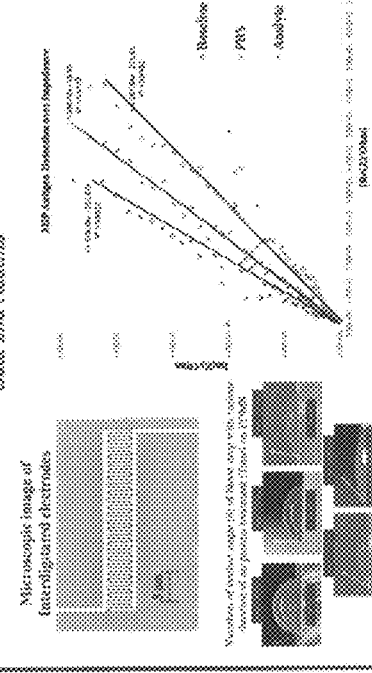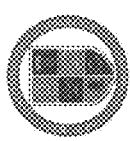
Figure 35

Fig. 45

Remember these basics

- MIPs have two components.
  - The STAMP that produces the cavities of the protein/molecule you want to FIND.
  - The Sensor complex that detects the changes in electrical properties the polymer undergoes when the antigen sterically binds to the cavities.
- The MIPs are EXPOSED to the blood/analyte.
- We are finding LARGE molecules (MW: 150,000 to 600,000). CA125 specifically is very large.

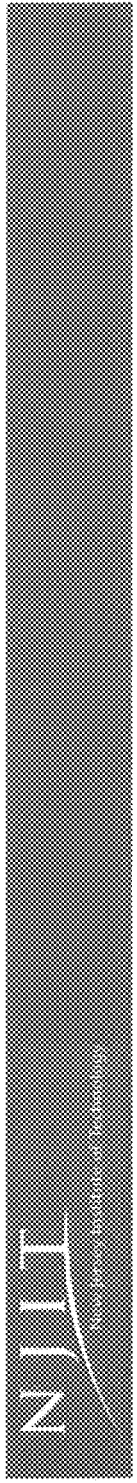

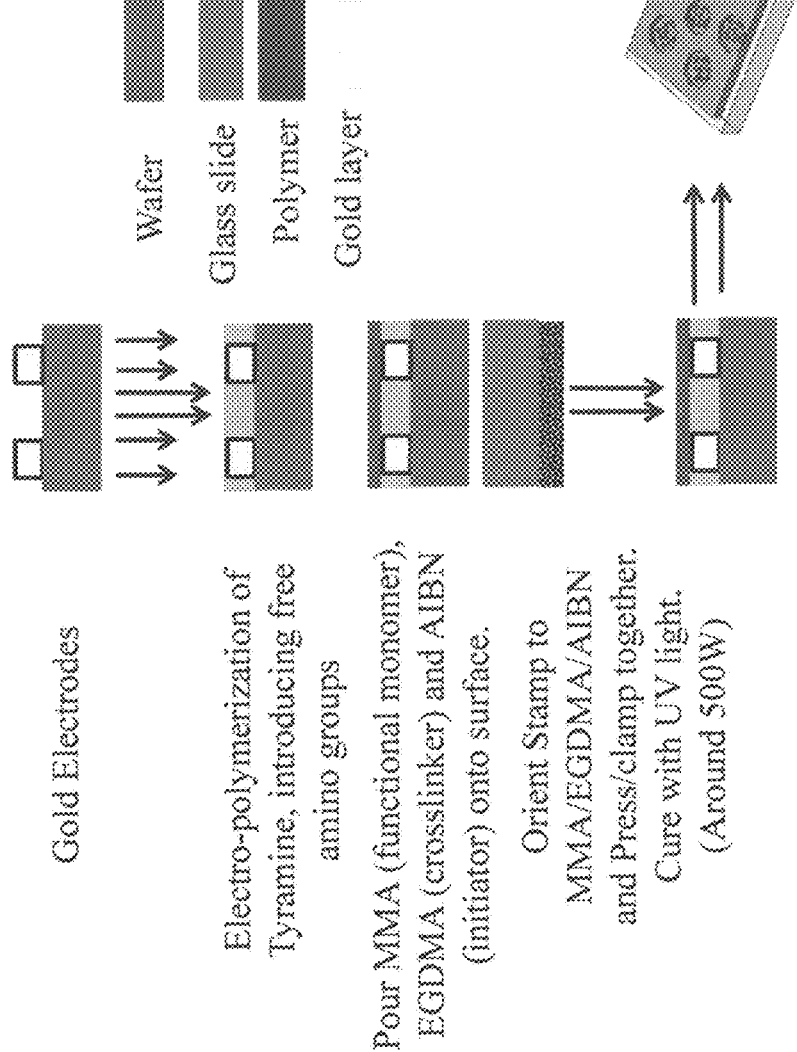

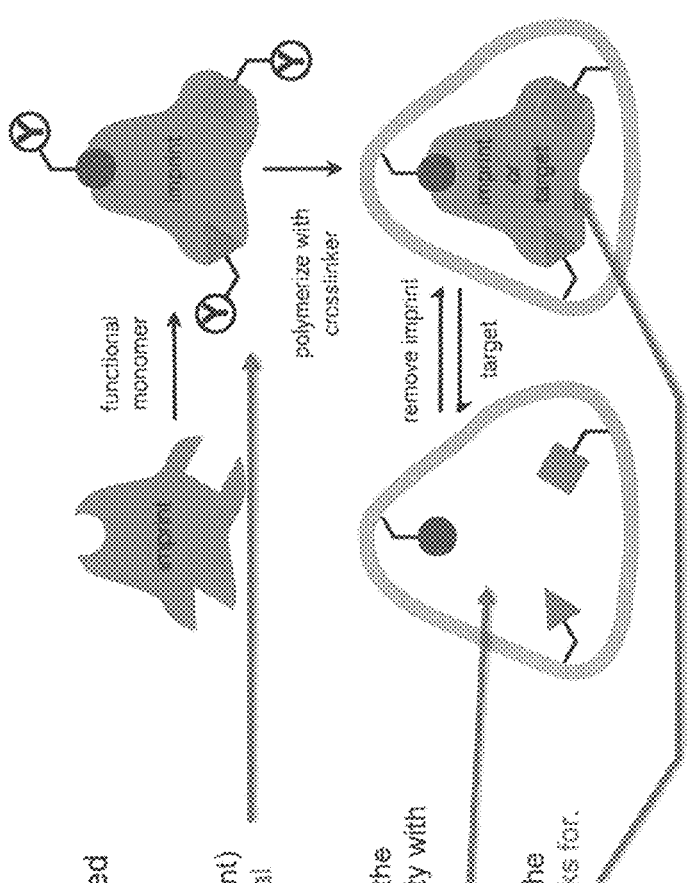

BIOMARKER DETECTION AND SELF-SEPARATION OF SERUM DURING CAPILLARY FLOW

CROSS-REFERENCE TO RELATED APPLICATIONS

The present application claims the benefit of the filing date of U.S. Provisional Patent Application No. 62/420,195 filed Nov. 10, 2016, U.S. Provisional Patent Application No. 62/420,226 filed Nov. 10, 2016, U.S. Provisional Patent Application No. 62/420,178 filed Nov. 10, 2016, the disclosures of which are hereby incorporated herein by reference.

FIELD OF USE

This disclosure relates to diagnostic assemblies to detect human diseases, such as cancer, and related pathogens. In particular, the present disclosure relates to a molecular imprinted polymer for biomarker detection using interdigitated electrodes in a biochip's microchannel having enhanced selectivity and sensitivity, and further relates to self-separation of serum during blood capillary flow through the microchannel.

BACKGROUND

Biochips are one technology currently under study to improve disease diagnosis. Biochips are defined as devices on which biomolecules such as DNA, proteins, sugar chains and cells containing these biomolecules are fixed in a large number, termed DNA, protein, glycochips and cell chips, respectively. Target molecules and compounds may interact with biomolecules on these chips that when analyzed may detect a disease state. However, the current state of the art biochips have many drawbacks. For example, diagnosis including screening and monitoring in the early phase after onset is difficult with current health check-up sensitivity and specificity. There is still a need to detect diseases such as cancers, lifestyle-related diseases such as hypertension and diabetes, and infectious diseases including influenza, rapidly, simply and accurately at a low cost using one drop of blood or test sample. Furthermore some biochips lack the ability to utilize other patient samples other than blood, for example other bodily fluids such as urine, saliva, spinal fluid, and the like. Also, some biochips are manufactured with glass that causes problems due to etching of the glass, cost of manufacturing, and extreme limitation of biochip construction. Use of other materials such as polymer based materials has failed due to the hydrophobic nature of the polymer material and its tendency for reducing the flow of any fluid.

The American Cancer Society stated that a total of 1,685,210 new cancer cases and 595,690 deaths from cancer are projected to occur in the United States in 2016. Cancer remains the second most common cause of death in the United States, accounting for nearly 1 of every 4 deaths. Most of the cancers are curable if they can be identified at earlier stages.

Ovarian cancer ranks as the fifth most common cancer in women and has the highest mortality rate among gynecologic malignancies. The early detection of cancers can enhance preventive measures, increase curability of the disease, reduces health care costs, and improves the quality of life for patients.

To achieve early detection of specific cancer types, highly sensitive and specific sets of biomarkers may be required. These cancer specific and early stage sensitive biomarkers can be substances that are expressed on cancer cells or created by the body's immune system in response to cancer cells. These types of biomarkers can be found in tissue, blood, or urine, and the detection of these specific cancer biomarkers in higher-than-normal amounts in the body may signify the presence of cancer.

Accordingly, an interest exists for improved diagnostic assemblies, and related methods of use. These and other inefficiencies need to be addressed and overcome as current assemblies, systems, and methods have many drawbacks as described above.

Thus, although biochip technology holds great potential for use in health monitoring systems around the world, and in particular in remote areas, there remain significant areas for improvement in the performance and ease of use of such technology. Complex disease diagnostics such as cancer diagnostics is still a nascent area of research that has not been completely explored by biochip researchers. Further improvement through study and development in this area is highly desirable.

BRIEF SUMMARY OF THE INVENTION

The above mentioned drawbacks are overcome and additional advantages obtained by the present disclosure. To achieve the early detection of a specific cancer type, the present disclosure includes a biochip that has a highly sensitive and specific set of antibodies and a sensing technology implemented. To increase the sensing capability, the biochip is fabricated with microchannels. The microchannel in the biochip is designed to control the flow mechanism and amplify the capillary effect of the blood flow. The flow is self-driven using the natural phenomenon called surface tension of the blood flow. Cancer antibodies with enhanced specificity and affinity are specially developed and ligated in the microchannel. When the blood sample flows in the microchannel over the cancer antibody, the cancer antigen from the blood forms antigen-antibody complex. This antigen-antibody interaction is captured using state of the art sensing technology and is developed using sophisticated nano circuit design in the biochip. The sensing methodology is a hybrid method of variation of capacitance charge. Also, the cancer severity is sensed depending on the intensity of the signal output. Therefore, the present disclosure can diagnose both the cancer and its severity using the micro biochip. Both qualitative and quantitative tests are used to test this novel sensing technology [1].

The novel state of the art sensing technologies applied in biochip can diagnose cancer both quantitatively and qualitatively. There are three ground breaking sensing technologies which are developed for cancer diagnosis, and also a hybrid method for implementing all these sensing technologies in the same chip is innovated to enhance its accuracy and reliability. The sensing technologies that are developed are: Temperature Variation, Variation Electric Oscillation, and Variation Capacitance Charge. Both cancer and its severity can be diagnosed using the micro biochip of the present disclosure.

The unique and exclusive characteristics of the biochip in sensing the antigen and antibody interaction are (1) the electrical sensing technology that is highly precise and accurate when compared to conventional optical sensing technology, (2) the quick response and instantaneous results with micro volume of blood sample, and (3) both qualitative and quantitative diagnosis of the cancer, which helps us diagnose the cancer with respect to each stage.

The capability of point-of-care (POC) biochip technology has the potential to revolutionize multiple fields of science and technology. The various science fields strongly impacted by biochip technology are microfluidics, nano technology, MEMS (micro electro mechanical systems) and micro fabrication field. This biochip research will also have numerous applications in disease diagnosis, drug delivery, organ-on-chip and lab-on-chip technologies.

The present disclosure makes the cancer diagnosis process a self-evaluation process. Therefore, anyone who needs to diagnose the existence and severity of cancer by a simple self-check process can receive an easy access to this POC biochip device directly from any commercial store and can perform self-check.

Molecular Imprinted Polymers (MIPs) for biomarker detection in micro and nano biochip are used as artificial antibodies in the diagnosis process of the complex diseases like cancer. The MIPs are fabricated with the desired sensitivity and specificity for individual disease diagnosis process. The MIPs are connected to the electrodes and the interaction of the biomarker with the MIPs can be detected using the electrical signal output.

The MIPs may also be fabricated to diseases not only restricted to cancer. The increased specificity and sensitivity of the MIPs can decrease the false negative and false positive scenarios in the diagnosis process. The MIPs can be sub layered with other bio molecules in order to expand the domain of diagnosis process to other diseases. The MIPs of the present disclosure may be used in the electrical sensing systems like identifying the variation in the electrical features, and also in the optical sensing systems.

Biomarker detection using interdigitated electrodes in the microchannel of the biochip is also utilized in the present disclosure. The disease biomarker may be diagnosed using the nanocircuit in the microfluidic environment. The interdigitated electrodes may be of different conducting materials. The coating of AG/AB may be of various diseases, such as cancer. The electrode dimensions are variable with respect to the capacitance generation. The intermediate layers between the electrodes and the AG/AB are fabricated using the coating on the electrodes with different materials like GOLD nano particles to enhance the sensing ability.

Intermediate layers also may include biomaterials along with the conducting materials like Bovine Serum Albumin (BSA) in order to increase the AG/AB interaction. The interdigitated electrodes are implemented in the microfluidic environment and specified shaped micro channels. The interdigitated electrodes are used to measure the capacitance change when the AG/AB interaction with biomarkers but the electrodes can also be used for other electrical measurements and variations.

Self-separation of serum during the capillary flow of blood through a microchannel of the biochip is also disclosed. The microchannel, depending on the implementation, is an individual channel and not a bifurcated channel. In some implementations the microchannel may be bifurcated splitting the segments. However, in this disclosure, the fluid is separated in the microchannel or channel itself without bifurcating it. The blood can be separated by itself using a unique design of the microchannel. The blood flows in the micro channel with no external pressure. The flow of blood in the microchannel is due to a capillary effect. The capillary flow of blood in a curved section of the microchannel experience forces like centrifugal force which separates the liquid from solid matters in the blood. The various viscosities or densities of the different segments in blood experience the different centrifugal effects while flowing through the curved section of the microchannel, which separates the serum from the blood.

The biofluid flow in the microchannel is due to intermolecular forces during a capillary flow in the microchannel by altering factors selected from a group consisting of: a size of the microchannel having a width between 50 μm to 1000 μm, and a depth between 50 μm to 500 μm; a surface morphology of the microchannel attained by physical surface treatments including nano patterning, etching, vapor deposition, lithography techniques, and any combination thereof; a chemical characteristic of the microchannel surface attained by chemical treatments including plasma treatment, etching, spin coating, and any combination thereof; a length between 0.5 mm to 100 mm and a design shape of the microchannel including serpentine, spiral, straight, and any combination thereof; and any combination of the above factors thereof.

The serum may be separated from various solid matter like red blood cells (RBCs), white blood cells (WBCs), and platelets of blood without using any external devices. The separation is instantly started soon after the blood flow in the microchannel. Self-separation of the serum in the micro channel can be implemented in various diagnosis process and significantly reduce the man power and efforts in the diagnosis process. The separation may be done when the blood flow in the microchannel, there will not be any need to external equipment to handle blood which limits the contamination. The separation of the serum from the whole blood does not require any sample preparation process.

The above objects and advantages are met by the present invention. Any combination and/or permutation of the embodiments are envisioned. In addition the above and yet other objects and advantages of the present invention will become apparent from the hereinafter-set forth Brief Description of the Drawings, Detailed Description of the Invention and claims appended herewith.

These features and other features are described and shown in the following drawings and detailed description. It is to be understood, however, that the drawings are designed as an illustration only and not as a definition of the limits of the present disclosure.

BRIEF DESCRIPTION OF THE DRAWINGS

The present invention will be better understood on reading the following detailed description of non-limiting embodiments thereof, and on examining the accompanying drawings, in which:

FIG. 22 is a chart showing variation in the contact angle of human blood with plasma treated PDMS for various durations plotted;

FIGS. 31-33 show steps in the fabrication process of the MIPs;

FIGS. 34-37 are presentations;

FIGS. 45-47 are slides relating to MIPs.

DETAILED DESCRIPTION

Figure 1:
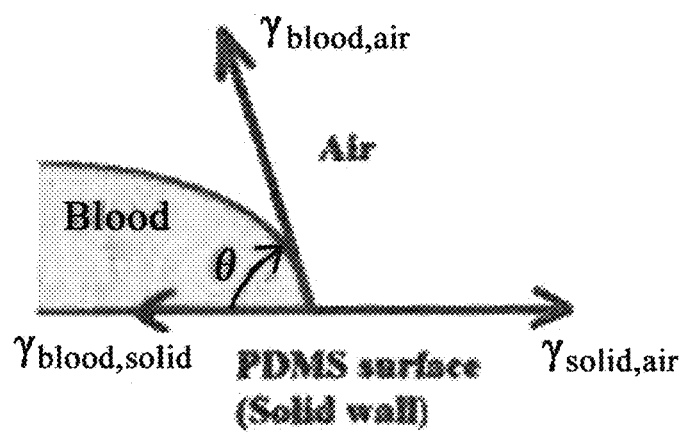
FIG. 1 is a schematic view of the blood drop on a PDMS surface with the interfacial tensions and contact angle.
Figure 2:
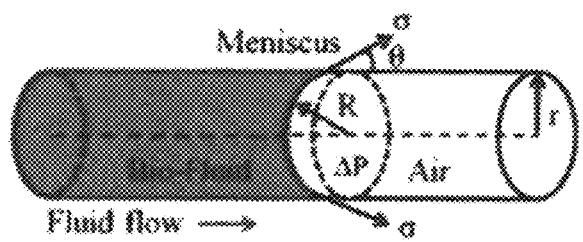
FIG. 2 is a schematic view of the biofluid flowing in capillary channel due to surface tension.
Figure 3:
FIG. 3 is a schematic view of the relation between the contact angle and the hydrophobicity of PDMS.

In general, the present disclosure overcomes the disadvantages of past attempts and provides several other advantages. In addition, it also overcomes the disadvantages of past attempts to detect disease-specific antigens. As used herein, "sample" refers to a sample from a mammalian patient. Non-limiting examples of a sample include tissue or bodily fluids. Bodily fluids can include blood, urine, saliva, spinal fluid, any combination of these, or any other fluid originating in the body. Where blood is referenced specifically, it is referred to merely for illustrative purposes and is in no way meant to limit the scope of the invention.

Point of care (POC) micro biochip serves to diagnose cancer at earlier stages with its innovative and state of the art 'sensing technology' to identify the existence of cancer antibodies in the micro volume of blood sample with no external devices and no sample preparation. Some of the features of the present disclosure are as follows: (a) Instantaneous results and without sample preparation requirement: The POC biochip is targeted to generate results below 120 seconds (after the bio fluid sample placed on the biochip) with the innovative electrical sensing methodology and the critical micro channel design. The sensing mechanism is designed to use bio fluid sample directly without any sample preparation requirement. (b) Self-evaluation tool: The POC biochip is a self-evaluation device, which functions by itself without any aid of external devices. The innovative designs of micro channel and nano circuit generate necessary forces and electrical charges required for the functionality of the biochip. Hence the biochip is portable and compact in size. Due to the ease of operation, the general patients can generate metrics for accurate diagnosis, prognosis and treatment efficacy. (c) Early detection of disease: The robust set of biomarkers that are specific for disease type significantly increases sensitivity and specificity, especially for early detection of disease from the population; thus, the diagnostic micro biochip can be used for both point-of-screening and point-of-care diagnostics tools. (d) Open system: The bio chip is an open system which can be utilized for diagnosing wide variety of complex diseases like multiple cancers, pneumonia, malaria and the like, by altering the corresponding bio markers and implementing the same sensing technology.

A continuous effort is being applied to enhance blood flow control in the micro channel without the aid of any external sources. To precision the biological and chemical reactions that are designed in the micro channel, the control of capillary flow of blood in channel is highly desired. Attaining better control on the blood flow in micro channel assists to open the doors for more innovative approaches in blood diagnosis like antigen [Ag] and antibody [Ab] interaction, separation of erythrocytes (RBCs), and the like. Enhancing the self-driven flow (capillary flow) conditions in micro channel can assist in avoiding requirement of the external equipment like syringe pumps to inject the blood into the micro channel. Minimizing the external equipment for creating the flow will decrease the blood flow volume which in turn helps in minimizing the requirement of blood quantity and controlling the contamination of blood sample. The capillary flow in micro channels is highly prominent due to their high surface to volume ratio. The capillary flow is generated due to the natural characteristics of surface of micro channel and fluid (blood) interaction. Capillary action is the resultant of both adhesion force (between the fluid and walls of channel) and the surface tension force. Surface tension is the tensile force attained by the interface due to imbalance of cohesive forces (attraction between the liquid molecules) of the molecules on the interface and the inner molecules. Adhesion (attraction force between the solid and liquid molecules) of blood with the surface of the micro channel causes the forward force at the edges. The surface tension holds the surface intact and contributes the whole liquid surface to move forward instead of movement only at edges. The surface tension quantifies the capillary phenomena.

The surface tension of the liquid (blood) depends on the contact angle. In simple terms, contact angle is the angle that liquid creates with solid surface, when both the liquid and solid surfaces come in contact. The internal balance of the cohesive forces (such as hydrogen bonds and Van der Waals forces) of liquid molecules and the adhesive forces (mechanical and electrostatic forces) of liquid and solid molecules, will define the contact angle created between the solid and liquid interfaces. As per the Thomas Young, the contact angle of a liquid drop on a solid surface is defined by the mechanical equilibrium of the drop under the action of the interfacial tensions. The three interfacial tensions observed when a blood drop is places on a solid (PDMS) surface are $\gamma_{blood,air}$, $\gamma_{blood,solid}$ & $\gamma_{solid,air}$, where the $\gamma_{blood,air}$ is the interfacial tension between blood and air, the $\gamma_{blood,solid}$ is the interfacial tension between blood and solid and, $\gamma_{solid,air}$ is the interfacial tension between the solid and air. As per Young's law, $$\gamma_{solid,air} = \gamma_{blood,solid} + \gamma_{blood,air} \cos\theta \quad (1)$$

From eq (1), the contact angle θ, can be calculated as per eq (2), $$\theta = \cos^{-1}\left(\frac{\gamma_{solid,air} - \gamma_{blood,solid}}{\gamma_{blood,air}}\right) \quad (2)$$

The surface tension causes a capillary pressure difference across the interface between two fluids (liquid and air). In a micro-channel of circular cross section with radius r filled with two immiscible fluids, the meniscus can be approximated as a portion of a sphere with radius R, and the pressure difference across the meniscus is:

$$\Delta P = \frac{-2\sigma\cos(\theta)}{r} \quad (3)$$

So altering the contact angle of the fluid with surface can help in controlling the flow, when the flow is a surface tension driven flow.

According to Lucas [3] and Washburn [4], there have been many experiments conducted on capillary flow. Over the recent times it is observed that the capillary flow is primarily dependent on the surface properties of the capillary channel. Surface properties of PDMS has been modified using with various methods such as coating of the inner walls of micro channel [5] attachment of active groups [6] thermal aging [7] plasma oxidation [8] and chemical coating [9]. However, oxygen plasma treatment has been used extensively by many in the fabrication of PDMS microfluidic devices in order to control the hydrophobicity. The treatment of oxygen plasma on PDMS introduces polar functional groups which is mainly the silanol group (SiOH). This group changes the surface properties of PDMS from being hydrophobic to hydrophilic. But behavior of blood flow on the surface treated channels gained the attention due to the variation of contact angle over the flow in channel, which thus influences the surface tension at meniscus and thus the flow field.

Surface treatment of PDMS (plasma oxidation): The surface tension gradient primarily depends on temperature gradient concentration gradient, electric field and modulation of the contact angle. The concentration of blood or the temperature of blood cannot be altered to preserve the natural properties of blood in the diagnosis research. Application of electric field in the micro channel involves the complex fabrication steps. So altering the contact angle is a source for controlling the surface tension and the capillary flow of blood in micro channel.

The micro channels are fabricated with the polymer (PDMS) which is by nature a hydrophobic surface (whose contact angle is greater than 90 degrees) which resists the wettability of fluid on the surface. For the liquid to flow naturally, a hydrophilic surface (whose contact angle is greater than 90 degrees) is required.

The hydrophobic nature of the PDMS can be altered to hydrophilic nature by performing various surface treatments like active group attachments, oxygen plasma treatment, thermal aging, and chemical coating. The surface treatments that include surface modification by exposure to energy do have lesser life time when compared to the other surface treatments. The surface treatments performed in the research are oxygen plasma treatment, addition of surfactant. The hydrophilicity attained by the surface treatment will sustain depending on the factors like temperature and humidity in which the PDMS mold is preserved.

Oxygen Plasma Treatment:

The oxygen plasma treatment to PDMS introduces the polar functional groups such as the Silanol group (SiOH) on the surface of PDMS. The silanol group is responsible for converting the PDMS property from hydrophobic to hydrophilic [10]. The oxygen plasma treatment also helps in increasing the adhesion property of the PDMS, so that it can be easily bonded with other substrates or another PDMS slab. But the surface treatment due to oxygen plasma treatment is not permanent. The hydrophobicity of the PDMS is retained back after some time (around 5 to 6 hours).

Figure 4:
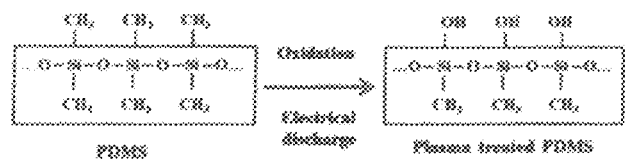
FIG. 4 is a schematic view of oxygen plasma treatment to PDMS.

A capacitor sensing mechanism to detect cancer antigens is disclosed. The approach is to setup an interdigitated electron based biochip sensor which is very compact and requires no cumbersome setups, as shown in FIG. 4. The surface to volume ratio is very high for this sensor enabling better sensitivity. An ultrahigh electrochemical interdigitated nano electrode biosensor has been developed by Zhu and Ahn for the detection of reversible redox species and has improved the detection ability by 100 times, compared with typical or conventional microelectrodes in the same sensing surface area [X. Zhu et al. 2005]. Laczka et al, 2008 shows if interdigitated features are comparable in size to the target analytes, the response is optimized. Interdigitated microelectrodes have drawn greater attention in the area of electroanalytical chemistry in recent years by showing higher sensitivities than conventional electrodes in electrochemical measurement. With the rapid development of nano fabrication techniques, nanoscale electrodes, especially nano interdigitated electrodes array (nIDA) have been utilized in various miniaturized electrochemical analysis systems for its desirable features and besides nanoscale provides better sensitivity compared to conventional electrodes (Gerven et al, 1998). Since the generated electric field by the nano electrodes are in between 100 nm that matches the region of interest, interdigitated electrodes are introduced to improve the sensitivity. In addition, the space confinement between the nano distances minimizes the noise (Jeong et. al, 2005).

In their simplest configuration the electrodes of a capacitance type sensor are two close-spaced parallel plates. Therefore, the capacitance between the two electrodes is given by $$C = \varepsilon_r \varepsilon_o \frac{A}{d},$$

where $\varepsilon_o$ is the vacuum permittivity and $\varepsilon r$ is the relative permittivity of the material between the plates. A is the electrode plate surface area and d the plate distance. From this equation it is evident that a change in the capacitance of such a device can be inflicted only in three ways: (i) by altering the distance d between the two plates, (ii) by altering the overlapping area A between the two plates and (iii) by a change in the dielectric permittivity between the plates. For the simplified case where the interdigitated electrodes are thick and where edge effects may be neglected, the capacitive expression is given by $$C_{sensor} = \eta\varepsilon\frac{lt}{d},$$

where $\varepsilon$ is the permittivity of the sensitive coating film, n the number of the fingers, l the length, t the thickness of the interdigitated electrodes and d is the distance between the electrodes.

Fabrication steps of the micro biosensor: The interdigitated electrodes are patterned on silicon dioxide (substrate) using general 'image reversal technique' or photolithography. Metal layers are patterned using dual tone photoresist AZ5214E. In the present disclosure, 2-3 μm of photoresist is used to create an inverse pattern of the desired design. Approximately 20 nm layer of titanium is spread over the surface by DC sputter deposition. The purpose of it is to improve the adhesion of gold on silicon dioxide film. Near about 180 nm of thick gold layer is deposited above and a lift of process is done. It is done by washing photo resist in pure acetone. Interdigitated electrodes having 25-30 fingers are patterned. At beginning, blank measurements are taken using Network Analyzer before the proper experiment. In next step, coating of electrode surface with Self-Assembled Monolayer is done. Thiourea was used as our SAM layer. The SAM layer formation is confirmed by checking with FT-IR. Preparation of Bovine Serum Albumin modified Gold nanoparticles is done. Nearly 3 ml of Bovine Serum Albumin is added into 30 ml of gold colloidal mixture and stirred for 20 hours to make Bovine Serum Albumin interact with gold nanoparticles. Near about 8-10 hours of incubation of modified gold nanoparticles onto the interdigitated electrodes is done followed by surface activation. Immobilization of the probes is done by incubation sensor platform in PBS buffer solution of antibodies for an hour and after that the binding of analytes takes place.

The values of dielectric changes for a tested biomarker because of the nature of analyte, size of analyte and its charge on the surface combined with the area of the interdigitated electrodes (Pethig and Kell, 1987). The electric field lines produced by the interdigitated electrodes penetrates through the medium, whether parallel or coplanar way.

In the development of a biosensor on interdigitated electrodes, various layers of chemicals are coated over it that subsequently increases the probe layer thickness. In addition, all the biological samples that are to be tested have an arrangement of electric charge carriers. The charges in the biological samples are displaced by the electric field and polarized to neutralize the effect of the external electric field. With this phenomenon, the dielectric of each analyte over the frequency spectrum has its unique characteristics. S-11 parameter network analyzer is used for electrochemical measurements.

The S-11 parameters are measured at 4 different stages of surface modification processes. At first stage, blank measurements were done for checking the working condition of the interdigitated electrodes to design the experiment. Secondly, after the SAM and modified gold nanoparticles layering. In the third stage, measurements takes place after antibody immobilization and finally after antigen/target binding on the interdigitated electrodes immobilized with antibody. The sensor platform is to be scanned as per the desired frequency (preferably 5 oMhz-1 Ghz) followed by inter-assay analysis. Impedimetric components are to be extracted from S-11 parameters for analysis. Based on these measurements, capacitance changes due to antigen binding are compared.

When the bio fluid flows through microchannel, the disease specific antigens in the bio-fluid interacts with the antibodies which are immobilized on the surface of electrodes and forms the antigen-antibody complex. The capacitance change due to antigen antibody interaction is measured between the interdigitated electrodes. This change in capacitance provides information of existence disease antigens concentration in the bio-fluid. The capacitance change due to antigen antibody interaction is measured between the interdigitated electrodes. This change in capacitance provides information of existence disease antigens concentration in the bio-fluid. The biosensor mechanism developed in the POC biochip can avoid the false positive and false negative scenarios, due to high sensitivity and specificity of the diagnosis.

While the present disclosure discusses the use of specific compounds and materials, it is understood that the present disclosure could employ other suitable materials. Similar quantities or measurements may be substituted without altering the method embodied below.

The primary steps involved to fabricate PDMS microchannels in biochip are fabrication of silicon wafers with micro channels, PDMS mold fabrication using Si wafer, and surface treatment of PDMS.

A silicon wafer of 4 inches diameter and 1 mm (An ample Si-wafer thickness (1 mm) is chosen, since the channel structures are etched from Si wafer which are 100 um to 200 um height) is used to fabricate the micro channels on it.

A silicon wafer of 4 inch diameter is cleaned well with acetone, isopropanol alcohol and DI water. Wafer is dehydrated at 115° C. for about a min using a hot plate and then kept on cold plate to attain normal temp. A negative photoresist (SPRTM 955) is deposited on the top of the wafer. The negative photoresist is used in order to remove the material other than the channel area. Si wafer which is coated with photoresist is placed on a spin coater using a specific size chuck and rotate the spin coater at 1200 rpm (can be changed to 2000 rpm, upon requirement) for a min, which will remove the excess photoresist, leaving the thin layer of (micro meters) of SPRTM 955 on wafer. Coated Si-wafer is placed on the UV light exposure tool (Karl Suss MABA6) with exposure time as 14 sec. Due to UV rays exposure, the area which is not covered by mask will become soft. The wafer needed to be treated with CD-26 chemical and DI water in order to remove the photoresist existing on wafer on the UV exposed area. Wafer is then dried with nitrogen gun to remove any water content.

A Deep Reactive Ion Etching (DRIE) which is also called the Bosch process is processed to etch more depth (107 um). The Si wafer is etched except at the channels which are covered by the photoresist, so that the channels are formed. The height of the channels attained is 107 um.

PDMS Base is blended with curing agent in proper proportion (1:10). Thorough mixing (about 10 minutes of whisking) is needed to make sure that the curing agent is uniformly distributed. This will ensure that the final PDMS mold is uniformly cross linked between base and curing agent. Degassing is performed multiple times so that all the air bubbles trapped in the PDMS mixture are removed. Curing of PDMS primary depends on curing temperature and time. The temperature of curing is indirectly proportional to the curing time. The PDMS is cured at 100° C. for 35 minutes. When PDMS is suitably cured, application of a steady pressure should help peal of the PDMS completely with ease.

Though PDMS is a soft material, still punching a hole at the inlet and outlet of the micro channel is a critical due to the micro dimensions. So a micro hole punching machine (Central Machinery, 5-Speed bench drill press) is used to make holes in the PDMS mold. These holes act as inlet and outlet for the micro channels. The PDMS molds are treated with plasma and pressed against glass or another plain PDMS slab in order to form the closed micro channels.

Figure 12:
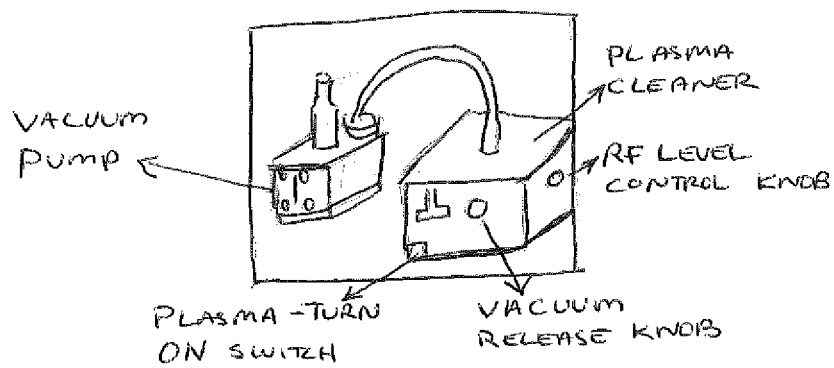
FIG. 12 shows oxygen plasma treatment equipment.

PDMS surface is highly inert and hydrophobic in nature. To convert the PDMS to hydrophilic the PDMS is exposed to oxygen plasma for various durations. In this experiment the hydrophilicity of PDMS is measured with duration of the plasma treatment. All plasma treatments are conducted on the 'Plasma Cleaner PDC-32G' with oxygen flow rate of 20 sccm and 100 bar pressure. The radio frequency (RF power supply of 150 W) of 13.56 MHz frequency is used for plasma excitation. FIG. 12 shows the plasma treatment equipment used for the experiment.

Figure 13:
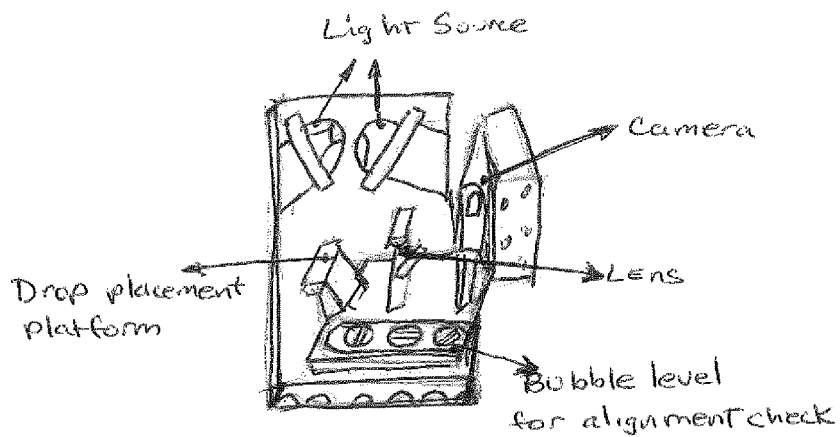
FIG. 13 shows the setup for taking image in order to measure the contact angle.
Figure 14:
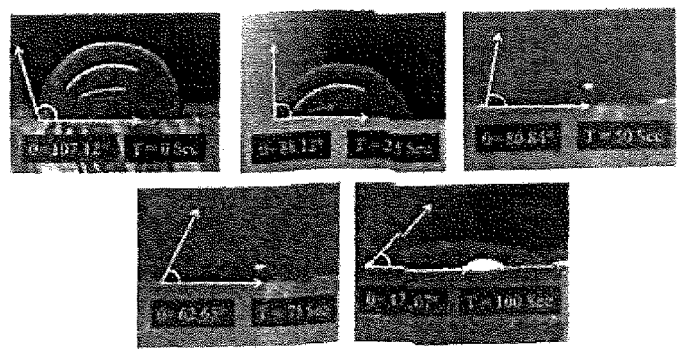
FIG. 14 shows images of blood drop (4.2 ul volume) on PDMS surface treated with oxygen plasma for various durations (0 sec, 25 sec, 50 sec, 57 sec & 100 sec)
Figure 15:
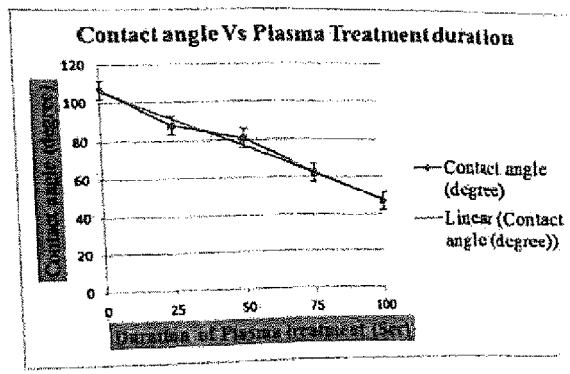
FIG. 15 is a graph of contact angle made by the blood drops on PDMS surfaces treated with oxygen plasma for various durations (0 sec, 25 sec, 50 sec, 57 sec & 100 sec)
Figure 16A:
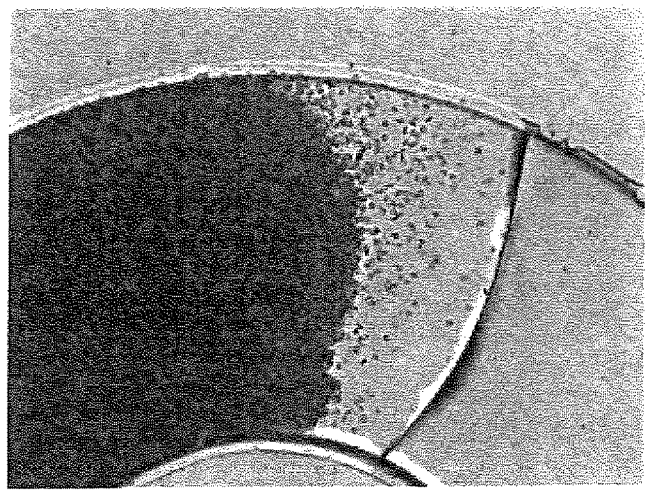
FIGS. 16A and 16B show images of human blood flow in the straight section and curved section of PDMS microchannel of 200 um width and 107 um height.
Figure 16B:
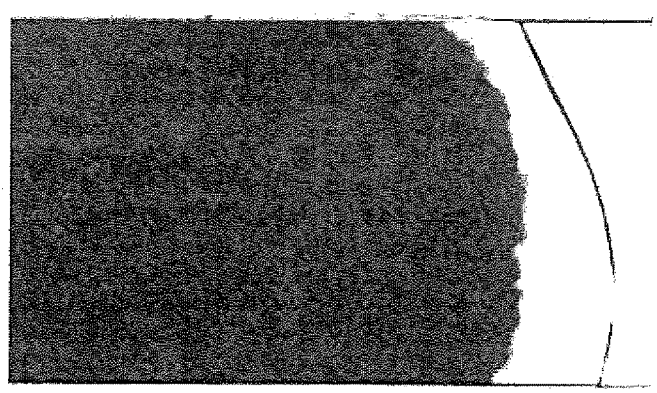
Figure 17:
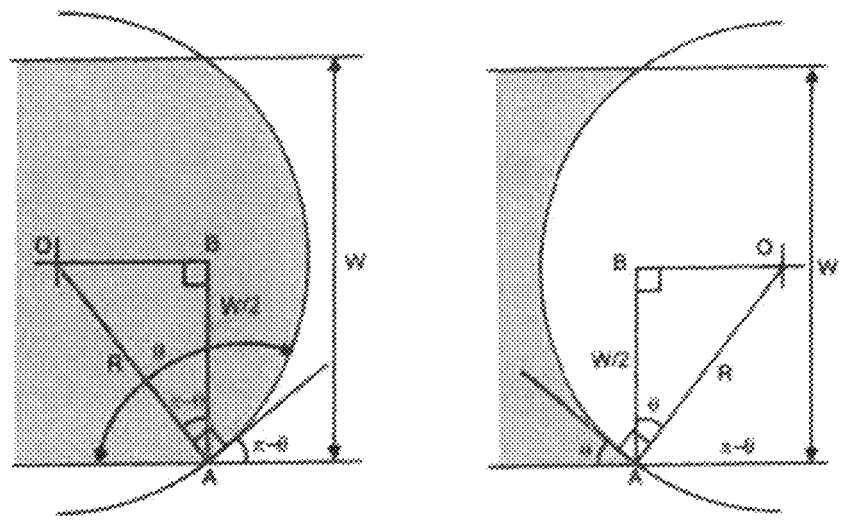
FIG. 17 shows a hydrophobic case, where θ>90° (Left) & Hydrophilic case, where θ<90° (Right); geometry of blood/air meniscus (gray represents blood)
Figure 18:
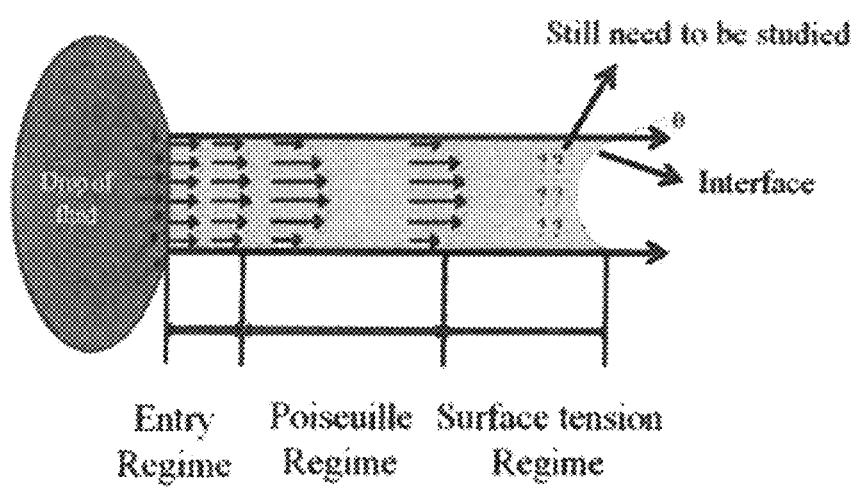
FIG. 18 shows surface tension driven flow field variation in the straight section of micro channel.
Figure 19:
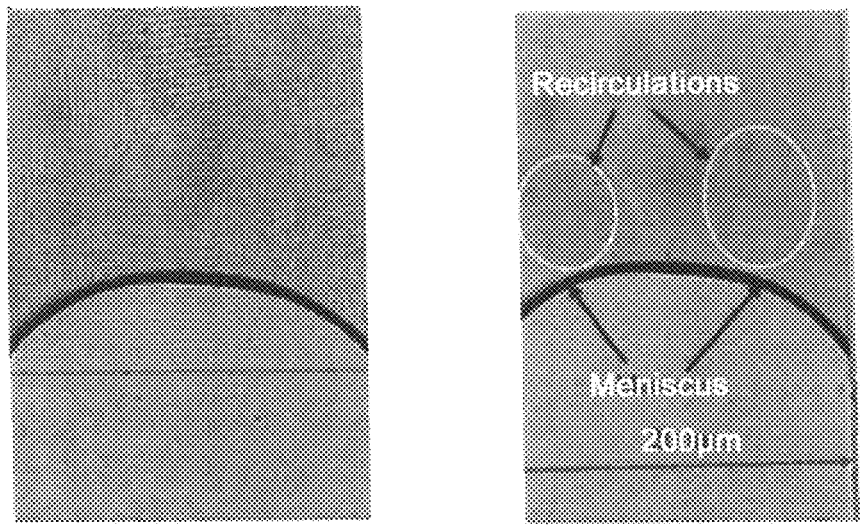
FIG. 19 shows flow field variation in the straight section of micro channel beside the meniscus & PIV vector notation of the flow field at the meniscus of the capillary flow in micro channel.
Figure 20:
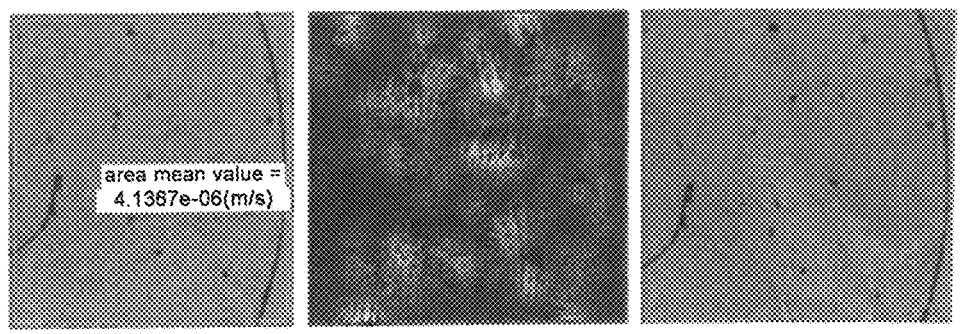
FIG. 20 shows capillary flow of ethanol with tracer particles in the curved section of the microchannel & PIV vector notation of the flow field of the capillary flow in micro channel.
Figure 21:
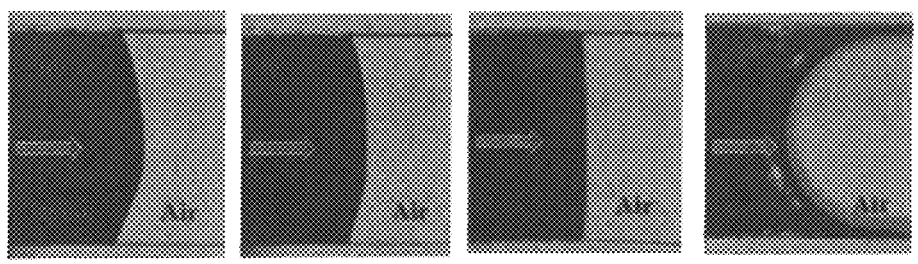
FIG. 21 shows images of human blood flow in microchannel of 200 um width and 107 um depth. The duration of channels treated with oxygen plasma are 200 seconds, 400 seconds, 600 seconds & 800 seconds.
Figure 12:
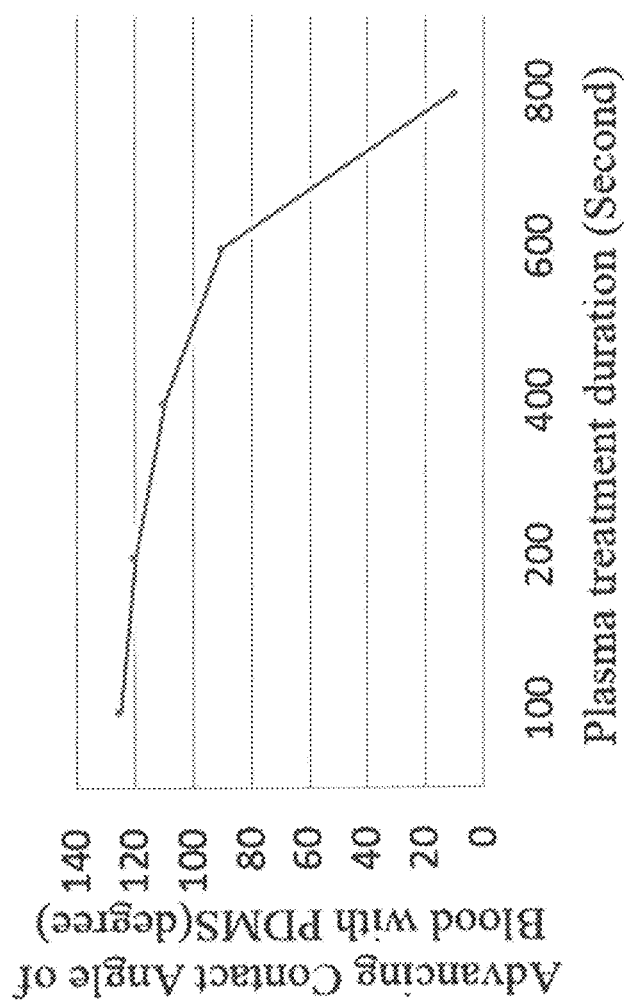

Contact angle variation of the bio-fluid drop due to surface treatments: The contact angle measurements are done using the custom made contact angle measurement system which developed by Guillaume Lamour and Ahmed Hamraoui. This setup consists of optical lens with a 50 mm (Thorlabs, BK7 A-coated plano-convex lens, 25.4 mm diameter) and a Sony cyber shot digital camera (8 mega pixels resolution). The contact angle measurement setup is shown in the FIG. 13. The static contact angle measurements are made based by sessile drop technique. Standard "Image-J" software is used to measure the exact contact angle from the captured images. All the corresponding contact angle measurements are repeated for 8 times to check the consistency. The contact angles measured accordingly achieved a precision with an experimental error of ±2° of variation with the theoretical values.

Considering the blood properties and the capillary length (capillary diameter of drop) is determined. The capillary diameter is determined by the below equation.

$$\lambda_{blood} = \sqrt{\frac{\gamma_{blood}}{\rho_{blood} g}} \quad (4)$$

As per Hrncir and Rosina [11] the surface tension of blood (γblood) at 22° C. is 55.89×10-3 N/m and the density of the blood (ρblood) is 1060 kg/m3. The acceleration due to gravity (g) is 9.81 m2/s. So the capillary length of the blood ($\lambda_{blood}$) is 2.31 mm. So the blood drop volume considered is 4.2 ul, (whose radius is 1 mm if the drop shape is assumed to be sphere). The diameter of the blood drop sample (which is 2 mm) was made sure that it is less than the capillary diameter of blood (2.31 mm).

The assumptions made while measuring the contact angle are: [a] the roughness factor of PDMS is ignored, so that the contact angle variations were made just by the surface properties instead of the roughness effect. [b] The values of $\gamma_{blood,air}$, $\gamma_{blood,solid}$ & $\gamma_{solid,air}$ are assumed to be constant throughout the experiment. [c] The surface tension of the blood is higher than the surface tension of the PDMS with surface treatments. [d] The PDMS sample fabricated are supposed to be rigid, smooth and homogenous. [e] The blood coagulation is not considered and the duration of the experiment is 100 seconds.

The contact angle is varied with the various surface treatments. The contact angle of the blood with the PDMS sample had decreased from 107.12° to 47.07°. The increased duration of oxygen plasma treatment to PDMS samples decreased the contact angle made by blood drop with the PDMS surface. This implies that the PDMS surface is converted from hydrophobic to hydrophilic with the oxygen plasma treatment [12].

The whole blood consists of formed elements that are suspended in plasma. About 45% by volume of whole blood consist of formed elements and about 55% of plasma in the normal human blood. The formed elements of blood are red blood cells (95%), white blood cells (0.13%) and platelets (4.9%). The diameter of red blood cell is about 8.5 μm at the thickest portion and about 1 μm at the thinnest portion. The viscosity of blood and plasma varies with samples due to the variations in species as well as in various constituents like protein and red blood cells between samples. Human plasma has a density of about 1035 kg/m3 and its viscosity coefficient ranges between 1.1 and 1.6×10−3 Pa s (the viscosity of water is 1×10−3 Pa s). The presence of plasma proteins results in the higher viscosity compared to water. Whole blood has a density of about 1060 kg/m3.

The flow behavior just beside the meniscus is yet to be defined as there are various force fields applied other than the shear stress and inertia forces by the fluid. The flow field is much different from the fully developed flow (poiseuille flow) to the flow field at the interface. The preliminary data of the experiment is as shown below. Understanding the dynamics of the fluid molecules at the interface due to capillary flow helps to understand the interaction of the molecules in the bio-fluids at the interface helps further in investigation of the controlling the bio-molecule flow movement in the capillary flow at various surface treated channels.

Blood flow in micro channels are needed to make a controlled flow to facilitate the antigen and antibody interaction. Since the capillary flow is the self-driven flow, flow controlling mechanism can be performed by varying the surface properties of the micro channel along with its shape and size. Some basic Newtonian flow experiments were performed in the PDMS micro channels. Flow in micro channel of 200 um width & 107 um with ethyl alcohol and tracer particles 8 um to understand the flow phenomenon using the micro PIV.

$$\theta = \frac{180°}{\pi}\cos^{-1}\left(-\frac{W}{2R}\right) \quad (5)$$

For hydrophilic case:

$$\theta = \frac{180°}{\pi}\cos^{-1}\left(\frac{W}{2R}\right) \quad (6)$$

The contact angle of the blood to the surface of the PDMS channel is evaluated with various durations of plasma treatments. The hydrophobic nature of the PDMS is converted to hydrophilic by the plasma treatment. The contact angle of blood can be measured using (eq3), when the surface is hydrophobic in nature. But when the surface turns to hydrophilic, (eq4) is used to calculate the contact angle. [2]

In the experiment, the capillary flow of human blood is measured in the microchannel of 200 um width. But the channels of the PDMS are treated with oxygen plasma with different exposure times. The various durations of the plasma treatment converted the PDMS surface to different levels of hydrophilicity which can be evaluated with the change in the contact angle of the human blood.

From the experimental analysis, it is understood that the longer the plasma treatment duration increased the hydrophilicity of the PDMS. But at the duration of 1000 sec there is no flow of blood in channel. The flow in the channel can be controlled efficiently with the apt duration surface treatment upon flow velocity requirement. Understanding the capillary flow behavior with respect to the surface treated microchannels is crucial to understand the capillary flow dynamics at various microchannels [13-14].

Study of bio molecule behavior at the meniscus of flow and also at various sections of the micro channels is important to enhance the bio-molecule reactions such as antigen-antibody interaction.

It is evident that the longer the plasma treatment duration increased the hydrophilicity of the PDMS. The duration of the oxygen plasma is indirectly proportional to the contact angle of the blood with the PDMS surface. So when the contact angle decreases the surface tension and the surface energy at the meniscus will increase.

The interdigitated electrodes are patterned on silicon dioxide substrate. Gold is used as the interdigitated electrode. Although there are various materials used as electrodes like aluminum, platinum, nickel and lead, but gold gives better sensitivity. Gul et al (2006) measured approximately 1-800 ng/ml antigen markers in interdigitated gold electrodes passivated by silicon dioxide layer. The next challenge in capacitive biosensor is immobilization of antibodies on top of the electrodes. Although there are many ways for antibodies immobilization using materials like semiconductors and metal oxides, Self-Assembled Monolayers (SAM) are the chemicals used for better immobilization and sensitivity (C. Berggren et al. 2001). Long chain alkanethiols are known to have insulating well organized structures on gold. Mirsky et al. 1997 have studied different immobilization methods of antibodies on gold. It was found that most promising method was based on activation of carboxy group on SAM molecules by N-hydroxy-succinimide.

Figure 23:
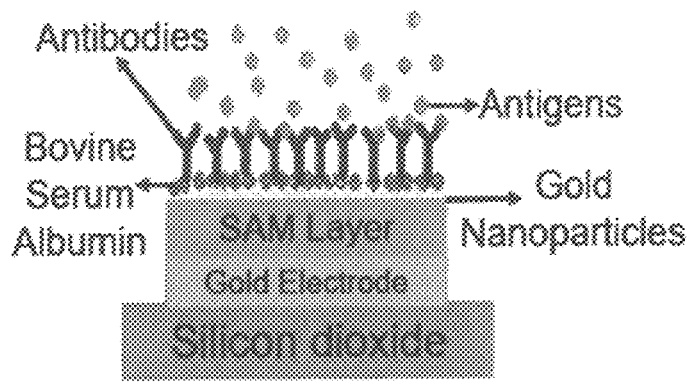
FIG. 23 is a schematic view of gold interdigitated electrodes on a polymer substrate with a polymer micro fluidics chip.

The biosensor assembly integrates the following elements: (1) interdigitated gold electrodes (2) self-assembled monolayer, (3) substrate, and (4) modified gold nanoparticles with bovine serum albumin, as illustrated in FIG. 23. Insulation of biorecognition layer is the major challenge faced by capacitive biosensor. (Berggren et. al, 2001).

Insulation is often superficial, implicating that ions can move through the biorecognition layer causing short circuiting. This is common occurrence when semiconductors or metal oxides are used as functionalized groups for immobilization of antibodies. Semiconductors and metal oxides also suffer from weak signal response. Self-Assembled Monolayer (SAM) is the functionalized group that overcomes these challenges. The SAM layer offers better electrode insulation which will lead to less noise and risk of short circuiting. In addition, SAM layer has stronger binding with the gold electrodes. Addition of SAM layer takes place over the top of patterned interdigitated gold electrodes.

A layer of modified gold nanoparticles is used on the SAM layer in the biosensor. Gold nanoparticles are used in the biosensor of POC biochip as they provide better stability for the immobilization of biomolecules on to the SAM. Nanoparticles surface can provide highly active and large surface area. Binding of very low target concentrations are possible. In modern biological and medical studies, gold nanoparticles have been widely employed, including genomics, biosensor, immunoassay, laser phototherapy of cancer cells and tumors, immune response enhancement, the targeted delivery of drugs and optical bio-imaging (EC Dreaden et. al, 2012). The improvement is due to the enhanced orientation facilitated by the gold nanoparticles binding to biomolecules allowing more freedom which is extremely useful when preparing label-free impedimetric biosensor. The primary characteristics of gold nanoparticles like high surface to volume ratio, surface energy and ability to decrease the distance between the proteins and metal particles are highly desired for better sensitivity of the biosensor.

The Bovine Serum Albumin (BSA) used in biosensor helps in increasing the specificity. Z. Zou et al. (2007) mentioned the use of Bovine Serum Albumin (BSA) for better specificity in detecting target protein molecule by blocking the surface. BSA prevents non-specific binding of the analyte to the surface, rather helps in flowing the analyte of interest.

Using BSA modified Gold nano-particles on the interdigitated electrode surface because it provides better stability for the immobilization of the probe or the biomolecules (Z.

Figure 24:
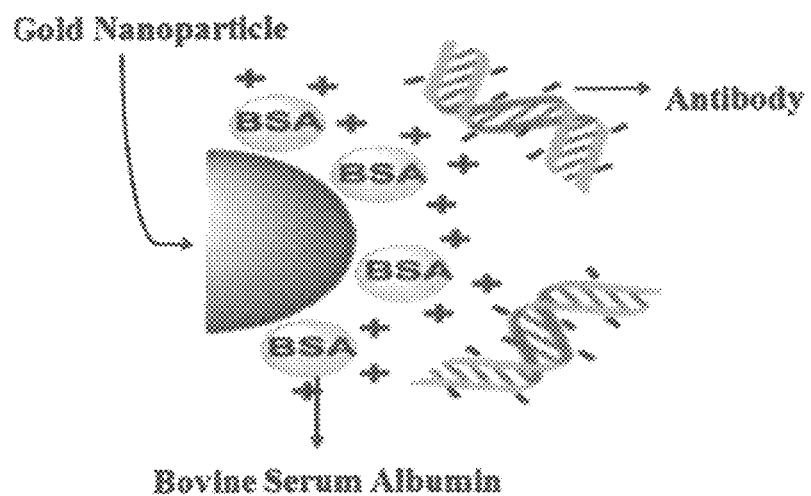
FIG. 24 is a schematic block diagram on the model of capacitive biosensor with BSA.
Figure 25:
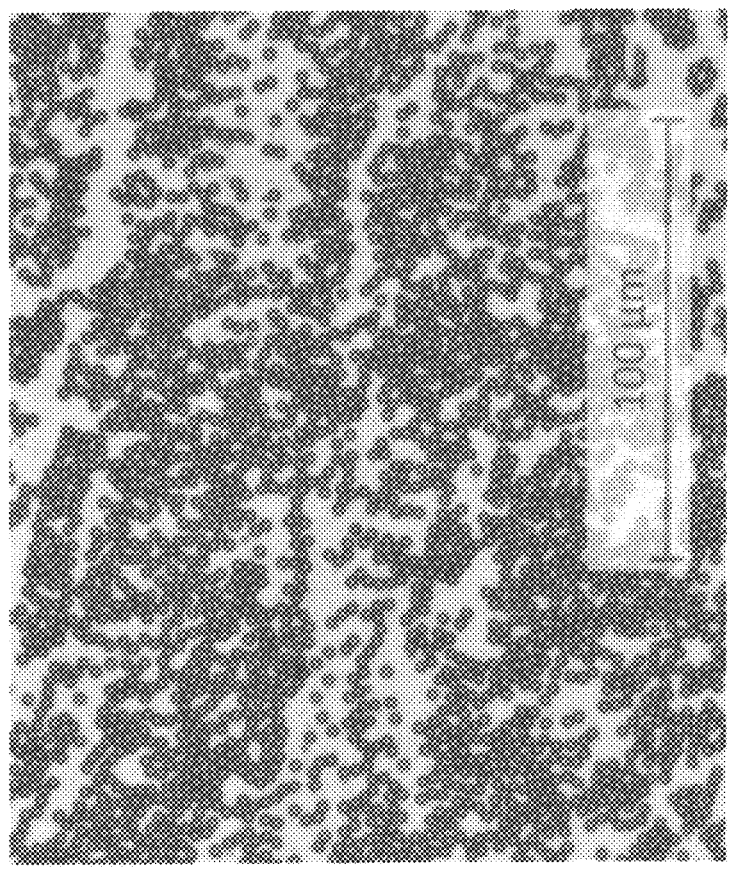
FIG. 25 are microscopic images of microchannel (200 um width) coated with dynabeads-M270 epoxy (coated with cancer specific antibodies)

Altintas et al. 2014). Antibodies are immobilized on top of the BSA—gold nanoparticles layer (FIG. 24). When the analyte binding takes place, the binding with the probes or antibodies gives rise to change in capacitance since both the antibodies and the analytes or antigens are charged molecules. The conjugate complex of Gold nanoparticles and BSA helps to have enhanced specificity and sensitivity that helps in early detection of disease. Thus, the cancer specific antigens can be detected in the human blood sample flow in the micro channel of the biochip with the capacitance (C) change.

Molecularly Imprinted Polymers (MIPs)—artificial antibodies: Molecularly Imprinted Polymers (MIPs) have proven potential as synthetic receptors in applications such as liquid chromatography to assays and sensor technology. Detection of cancer biomarkers requires sensitive and selective detection of analytes in the nM and pM range and cannot be currently satisfied in a platform that is portable, economical, while exhibiting high stability to chemical and physical conditions [19]. Creating highly efficient synthetic receptors for bio-recognition processes is considered to be in the nascent stages of development [20]. Molecular imprinting is one of the few general, non-biological methods for creating molecular receptors [21], [23].

Figure 26:
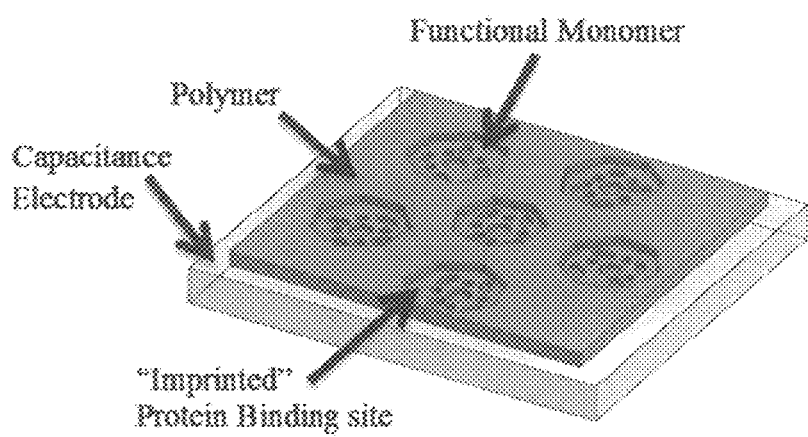
FIG. 26 is a perspective view of a molecular imprinted polymer system, showing a surface imprinting method, and MIP detection system components shown are: (1) the imprinted binding site is printed by natural antibodies; (2) the functional monomer retains the geometry, size and orientation of the antibody for non-covalent attraction; and (3) gold capacitance electrode to detect non-covalent binding.

At the core of MIP technology are recognition elements that bind to specific proteins from the analyte, as shown in FIG. 26. In particular, MIP technology involves forming a complex between an analyte, which serves as a template, and a functional monomer. A three-dimensional polymer network is formed with a cross-linking agent. After polymerization, the template is removed from the polymer. This step leaves specific recognition sites that are complementary in shape, size and chemical functionality to the template. The polymer recognizes and binds selectively only to the template molecules.

MIPs show promise as they offer a synthetic route to detecting a wide range of bio sensing recognition of macromolecules. Natural antibodies, receptors and/or enzymes are used in the laboratory setting as traditional detection methods for the target analyte. They are of limited use outside of a laboratory setting, as they are sensitive to temperature, pH, and organic solvents in addition to the high price or preparation difficulty. Unlike natural antibodies, MIPs are generally easy to manufacture, offer high stability, and can be tailor made when natural biological receptors are not available. In 2016, Wackerlig et al. stated that MIPs are a direct replacement for natural antibodies [23]. MIPs offer this functionality by either mimicking the function of the antibody or by copying the actual structure of the antibody. As such, MIPs are highly versatile as potential affinity biosensors; especially inconsideration to binding interactions between a bio-recognition element on a sensor chip and the analyte of interest.

TABLE 1

Current Immunosensor/Biosensor Detection Limits

| Method | Detection Limit (in ng mL$^{-1}$) |
|---|---|
| Electrochemical Immunosensor | 0.5 |
| Dark Field Microscopy | 4.5 × 10$^{-7}$ |
| Capacitive Immunosensor | 3 |
| Microcontact-PSA Imprinted Capacitive biosensor | 8.0 × 10$^{-5}$ |

The above Table 1—Current Immunosensor/Biosensor Detection Limits illustrates: (1) the current detection limits for various biosensors developed by the scientific community. (2) microcontact MIP providing very favorable detection limits within the target analyte.

Current CA-125 assays are variants of the enzyme linked immunosorbent assay (ELISA) where it is necessary to utilize enzymatic, fluorescent or chemiluminescent labeling. As a valuable biomarker, detection of elevated levels of CA-125 is a key part in ovarian cancer therapy. As part of the National Cancer Institute's (NCI) Prostate, Lung, Colorectal & Ovarian Cancer Screening Trial, CA-125 was determined to be the best biomarker, among 35 other candidates[24], [25]. Nominal CA-125 blood levels are less than 35 U mL and an absolute increase of 5 U/mL is highly predictive of disease.[26] Elevated levels of CA-125 are present in about half of women whose cancer has yet to metastasize and over 90% of women have elevated serum levels of CA-125 in advanced cancer. Thus, in order to facilitating early detection methods economically and reliably, methods for detecting CA-125 as a screening test must be explored.

In 2007, Wu et al. prepared a novel type of biosensor where CA-125 and horseradish peroxidase (HRP) was co-immobilized with CA-125 via immune-conjugation. Hydrogen peroxide, acting as an enzymatic substrate of HRP, was then released into the sensor allowing CA-125 to be measured by the electrode current produced by the HRP-catalyzed reduction of H2O2. Reported detection levels were 1.8 U/mL with a linear range between 2-75 U/mL [27]. Later, in 2009, a novel field effect enzymatic detection technique was utilized where external gating voltage induced an electric field at an enzyme-electrode interface in order to amplify signaling current of the enzyme-based biosensor. The technique lowered the detection limit of the analytes from 10-3 M to 10-12 M.[28] More recently, in 2016 Dick et al. identified a detection method on specific collision of a single murine cytomegalovirus (MCMV) on a platinum electrode [29]. This method relied on enzyme conjugation between the antibody and the virus to facilitate detection. As such, these approaches rely on enzymes that are sensitive to environmental, usage and storage factors and are as such limited in potential field deployment.

It is then important to introduce a label free detection method that can detect antigens without the need of enzyme conjugation. Indeed, in 2012, Viswanathan et al. was able to develop a protein imprinted MIP utilizing a three dimensional gold nano-electrode assembly [25]. The protein was applied to a thin film coating and upon extraction; imprinted sites with affinity to CA-125 were created. Viswanathan and his collaborators reported that under ideal conditions, the detection of MIP imprinted CA-125 was found within a range of 0.5 to 400 U mL-1. Interestingly, the analyte utilized in the experiment was spiked human blood serum along with unknown real serum samples. Viswanathan et al. mentions that the presence of non-specific proteins within the serum did not significantly affect the sensitivity of the MIP assay. Performance of surface imprinted polymers was improved by template immobilization on a core support before polymerization. This increased the number of homogenous imprinted cavities on the surface of an MIP film [30].

Sensing mechanism to detect the antibody and antigen interaction: Sensing mechanism is developed to sense the bio molecular interaction when the bio-fluid flows in the micro channels. The diseased antigens if exists in the biofluid interacts with the antibodies that are immobilized in the microchannel when the biofluid flow in the micro channel. The artificial antibodies-MIPs are used in the sensing mechanism in order to have the specific signal with no false positive and no false negative scenarios. The sensing mechanism developed should be able to implement using both natural and artificial antibodies (MIPs).

Figure 27:
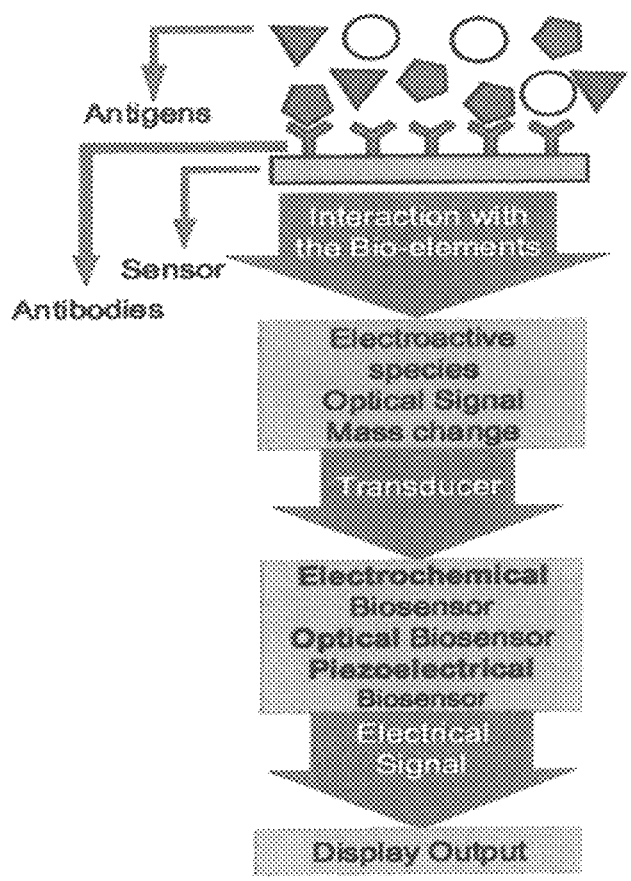
FIG. 27 is a block diagram of a biosensor and its components.

A biosensor is an analytical tool consisting of biologically active material used in close conjunction with a device that will convert a biochemical signal into a quantifiable electrical signal. A biosensor typically consists of a bio-recognition component, bio transducer component, which include a signal amplifier, processor, and display, as shown in FIG. 27. The main function of the transducer is converting the biomolecular binding to a quantifiable signal. The recognition component, often called a bioreceptor, uses biomolecules from organisms or receptors modeled after biological systems to interact with the analyte of interest. This interaction is measured by the biotransducer which outputs a measurable signal proportional to the presence of the target analyte in the sample. The general aim of the design of a biosensor is to enable quick, convenient testing at the point of care where the sample was procured.

Modern biosensors are based on sensing components and transducer components. Sensing components or bioreceptor interaction types can be enzymes, microbes, organelles, cells and tissues, Antibody-Antigen and nucleic acids. Good bioreceptor is designed in that way so that its interaction with specific analyte produces an effective measurable by the transducer. High selectivity among a matrix of biological component is the key requirement. Based on transducer components, biosensor can be classified majorly into Optical, Electrochemical and Piezoelectrical, as shown in FIG. 27. In present, optical techniques are widely used for the biosensing. In optical biosensors, the biological sensitive element is immobilized onto the surface of the transducer and the respond to the interaction with the analyte is withered by generating an optical signal, such as fluorescence or by undergoing changes in optical properties such as adsorption, reflectivity, emission and refractive index. The certain transducing techniques for optical based sensors are Interferometry, Total internal reflection fluorescence, Surface Plasmon Resonance and Surface enhanced Raman scattering. Surface plasmon resonance is one of the main optical biosensor technologies and has been the subject of numerous reviews (Mullett et al., 2000; Homola, 2003; Scaranoa et al., 2010).

The current researches on the biosensors are primarily based on the optical methodology which requires sophisticated and massive setup. The setup is expensive as well. The devices and methods of the present disclosure have a higher sensitivity within a small space and setup. The measuring methodologies of other sensors are quite difficult for certain non-electrochemical biosensors. The fabrication of the other non-electrochemical sensors are tough with respective to sensitivity. Optical sensors techniques faces great challenges in term of developing simple, portable and inexpensive setups and models. In optical techniques, periodic rinsing is often required to prevent biofouling and also, optical sensors are limited in laboratory because the fluorescent detection instrumentation is too bulky, lacking portability for point-of-care use.

In modern world various types of capacitive biosensors are used, such as interdigitated electrodes based, electrode-solution interface based and on capacitive membranes (C. Berggren et al. 2000). Berggren et. al, 1999 work states that electrode-solution interface based biosensors have the most interesting applications for DNA sensing. Electrode-Solution interface based electrodes have been used for detection of analytes in real human samples or complex matrices. Matrix interference for electrode-solution based capacitive biosensors occurs due to the unknown contribution of complex matrix biological specimens to the recognition layer and diffusion layer capacitances (Thompson and Ellison, 2005; Tosar et al., 2010). The changes in the capacitances in the recognition layer may be affected by non-specific binding which is a major drawback. The experimental methodology that involves passivation of the functionalized layer and use of reference electrodes may be employed to reduce the effect of interfering substances, but reliable biosensing in complex matrices is hard to achieve. (V. Tsouti et al., 2011).

Mass or piezoelectric based capacitive biosensor is another type used for detection of analytes. Surface stress based biosensors consist of flexible structures where one of their surfaces is functionalized with probe molecules. The interaction with the appropriate target molecules induces surface stress variations and finally changes in the deflection of the structure. In most cases, cantilever bending is detected by optical methods (Fritz et al., 2000; McKendry et al., 2002; Hansen et al., 2001). In addition, measurements are difficult in opaque medium such as blood. Piezoresistive detection is comparatively less sensitive and temperature dependent. V. Tsouti et al., 2011 mentions that mass based capacitive biosensors are complex and complexity varies as per the interaction. Capacitive micro machined ultrasonic transducer is mass sensitive based device in which the surface membrane is covered with sensitive layer and during the interaction with the appropriate analyte the element mass increases and the changes in frequencies are observed. These devices serve well in the chemical sensing applications but biological sensing is not yet reported promising (Park et. al, 2007). The obstacle for their use in biosensing is their immersion in the liquids. The vibrations of the cantilevers or membranes are hindered, causing damping effect. Mass methods or piezoelectric methods are very sensitive and suffer the non-specific adsorption which decreases the specificity. Besides, the detection, instrumentation for mass methods includes capacitive membranes, cantilevers or piezo-electric resonators in micro scales which are very costly and cumbersome.

First, study of flow control mechanisms in micro channels using surface treatment in surface tension driven flows. Second, is to develop molecularly imprinted polymers (MIP)—Artificial antibodies which are capable of rapid, portable, sensitive and label-free multiplexed bio molecular detection. The experimentally validated models will be used in the micro biochip to examine the disease diagnosis with respect to flow and the corresponding sensing mechanism. The MIPs that are developed are mimicked to complex diseases like cancers which will be helpful in diagnosis process. Finally, to develop a sensor platform based on capacitance model which is more sensitive, portable, robust and suitable for label-free cancer marker detection.

Kinetics of MLPs were pioneered by Whitcombe et al. where MIPs were successfully prepared with two analyte specific binding sites utilizing a thermodynamic analysis to understand the chemical equilibrium process [32]. Whitcombe determined equilibrium concentrations of the template molecule, the functional monomer and the concentration of the desired template monomer complex can be calculated from the following rate equation under certain assumptions:

$$[MTM] = K^2 \cdot [T] \cdot [M]^2 \quad (2)$$

Where K is the association constant between the MIP surface and the target analyte; [T] is the concentration of the template antibody; [M] is the concentration of the functional monomer, and [MTM] is the concentration of the desired template monomer complex. Li et al. (2012) stated two assumptions for this rate equation where the strength between both interactions of the two functional monomers and template molecule are identical; and two association events between two functional monomers and one template molecule are independent [33]. Li et al. then suggested additional assumptions to equation (1) such as: two-point binding force for the template molecules is very strong compared to one-site binding such that excellent selectivity can be achieved with low MTM concentration; No strong nonspecific interactions between the template molecules and the cross linked polymer chains; that the association constant K is the same in preparation and application [33]. The integration of these assumptions facilitates equation (8):

$$N=N_s+N_{NS}=P\{K^2\cdot[MTM]\cdot+K\cdot[L]\cdot([M_0]-2[MTM])\} \quad (8)$$

Where the total binding (N) is the sum of the specific ($N_s$) and non-specific ($N_{NS}$) bindings. The polymer concentration factor (P) is in relation to the concentrations of the template molecules and the polymer. With equation (2), Whitcombe et al was prepared MIPs where the K value was calculated with chemistry software and verified experimentally through chromatography, spectroscopy, and NRM [33].

Thermodynamic analysis of MIPs was pioneered by Jencks et al in 1971. Then in 1991, Williams et at presented a thermodynamic equation relating Gibbs free energy with translation, rotation and other molecular properties[33]-[36]. Then in 1995, Nicholls et al. streamlined the work done by Williams et al. and introduced a refined thermodynamic equation (9)[37], [38]:

$$\Delta G=\Delta G_{translation+rotation}+\Delta G_{rotors}+\Delta G_H+\Sigma\Delta G_t+\Delta G_{vdw} \quad (9)$$

Where ΔG is change in Gibbs free energy on the formation of the monomer-template complex; $\Delta G_{translation+rotation}$ is the change in translational and rotation Gibbs free energy; $\Delta G_{rotors}$ is the change caused by restricted rotation motion of the template molecules. $\Delta G_H$ is the change caused by hydrophobic interactions; $\Sigma\Delta G_t$ is the change caused by whole group reactions; and $\Delta G_{vdw}$ is the change caused by van der Waals forces [33].

Figure 28:
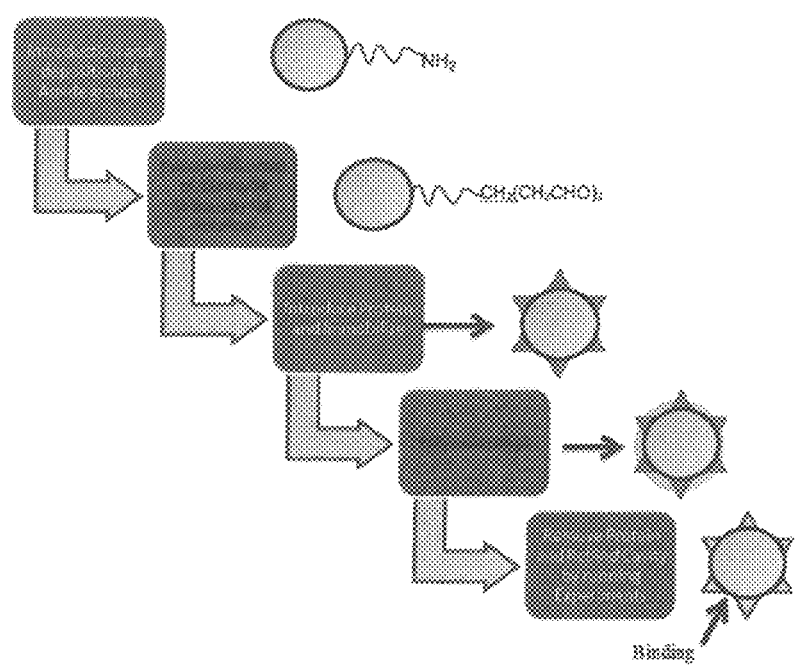
FIG. 28 shows a generalized process chart for creating MIPs.
Figure 29:
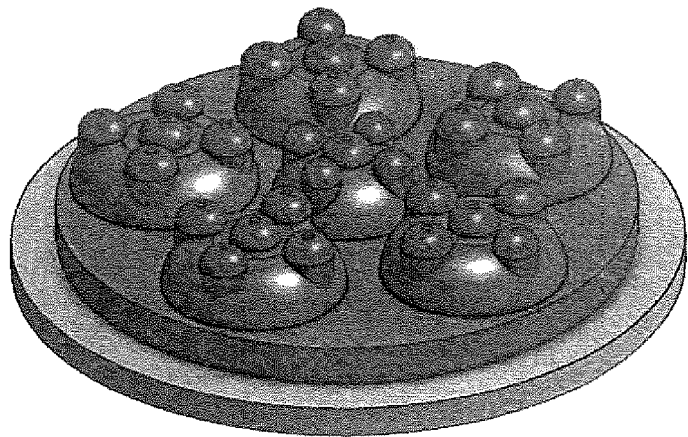
FIG. 29 shows a MIP mold with specific biomarker definition thereon.

The scientific improvements to MIP detection specificity can be made by adequately choosing the appropriate method of manufacturing. There are five main components to surface imprinted MIPs where (1) a template is used to imprint a protein shape on to (2) a functional monomer. (3) A cross linker is then utilized to fix the functional monomers around the template molecules by forming a highly rigid polymer through (4) a polymerization initiator. Any remaining protein on the film surface of the MIP is dissolved through (5) a biocompatible porogen solvent. Refer to FIG. 28 for process chart and overview of this process. In a five-step process, amino groups will be introduced to the template surface, which are followed by aldehyde groups via reaction of amino, and glutaraldehyde. Polymerization. of the PDMS occurs after the antibody is immobilized onto the amino groups and introduced to the PDMS substrate. Post polymerization, the template will be removed leaving specific binding sites for the target (antigen) protein at the surface of the PDMS material. Previous methods included the Bulk polymerization which until recently was the most generalized technique due to its simplicity ease of manufacturing [39]. However, this method is characterized with only a 30-40% of polymer yield with particles being of irregular shape due to grinding, offering poor binding characteristics as high affinity sites are destroyed[20], [22]. Poor protein rebinding characteristics were attributed to long diffusion distances. By utilizing MIP nanoparticles, the surface area to volume ratio of was improved [23].

An improvement to bulk polymerized MIPs is suspension polymerization utilizing liquid perfluorocarbon; however this method is not economical[20]. Precipitation polymerization holds promise as a viable alternative; however, the process has several issues including utilization of a large volume of porogen (about 50% wt). This led to cost increases compared to alternatives. In addition, precipitation polymerization requires a long polymerization time in order to generate the necessary shapes and cavities[20], [22].

Thus proposing economical, alternative strategies aimed at improving the yield of effective binding site complexes must be a focus of future research. Surface Imprinted. MIPs are not a new concept but their manufacturing can be incredibly varied depending on the application [30]. By focusing on surface imprinting, specifically epitope mediated and micro contact imprinting, the biosensor can be specially suited to detect many types of antigens along the micro channel. When an antibody attaches to an antigen, the interaction occurs at a small characteristic substructure establishing a recognition site. Thus the entire bio-molecule is not needed to identify the antigen[20]. This surface imprinted method is an improvement to previous methods and offers much higher sensitivity and specificity and traditional methods[23].

Figure 30:
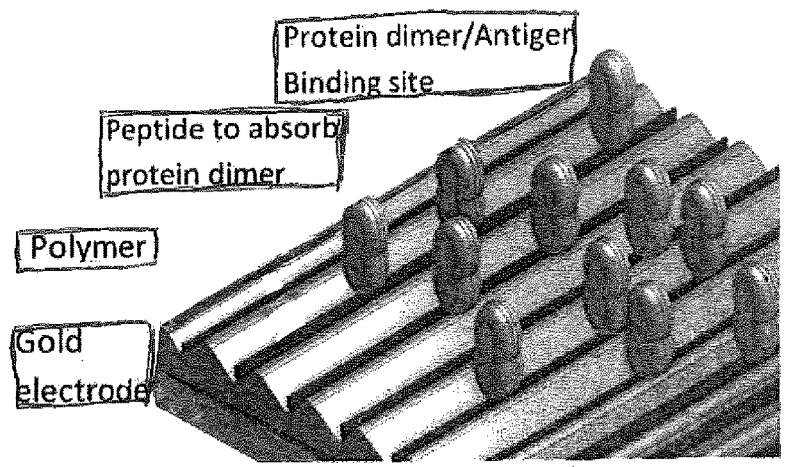
FIG. 30 shows an epitope mediated MIP: (1) A gold electrode is utilized for capacitive measurements as they are the most sensitive (Mattiasson et al. 2016). (2) Polymer utilized to hold the peptide. (3) Protein dimmer which is highly selective to target protein/analyte.
Figure 31:
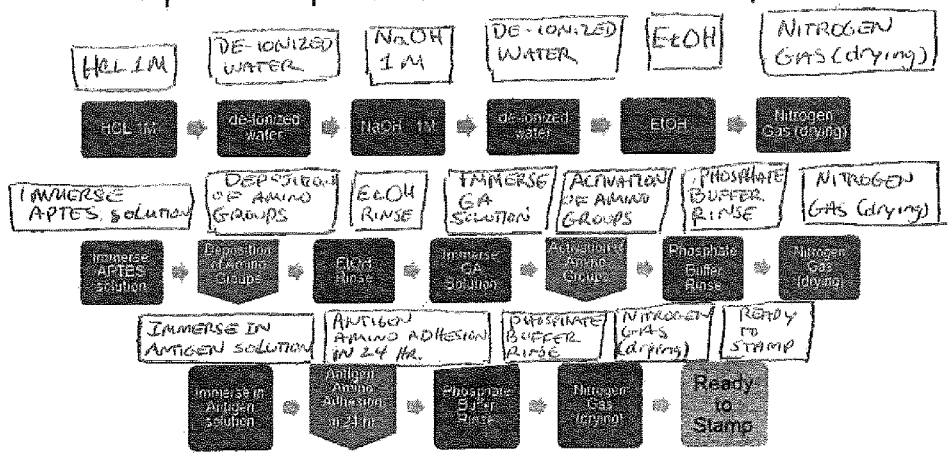
Figure 32:
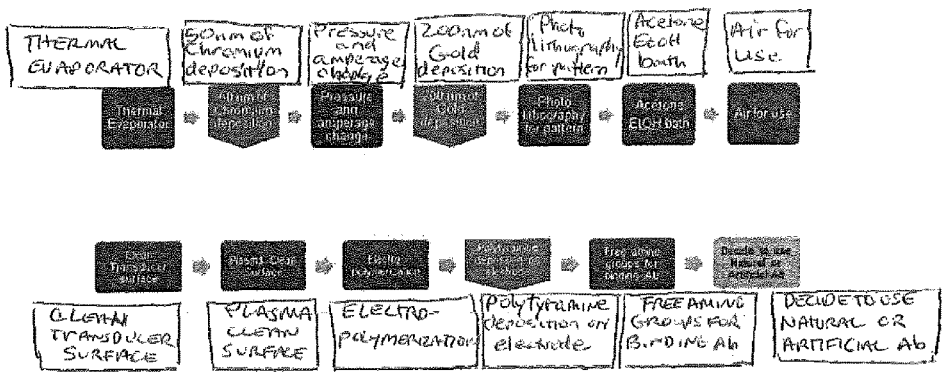
Figure 36:
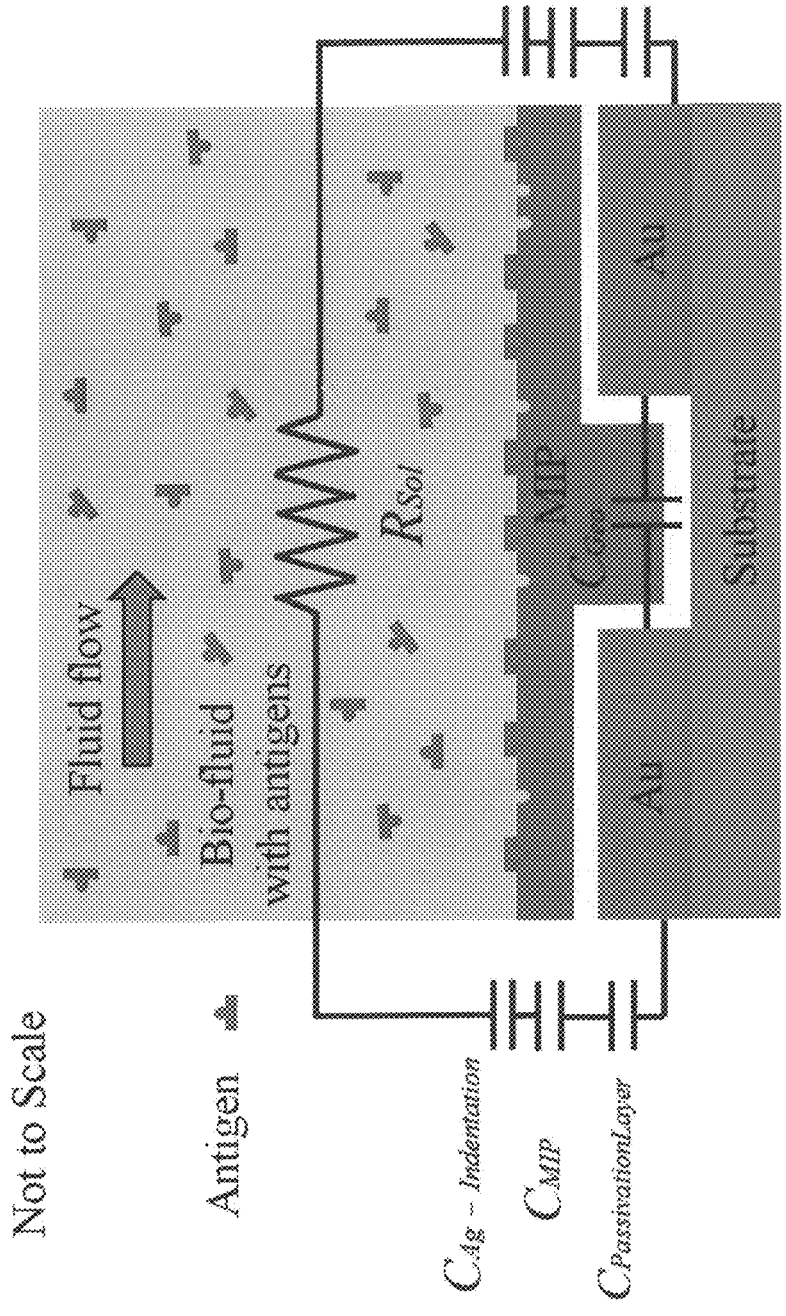
Figure 37:
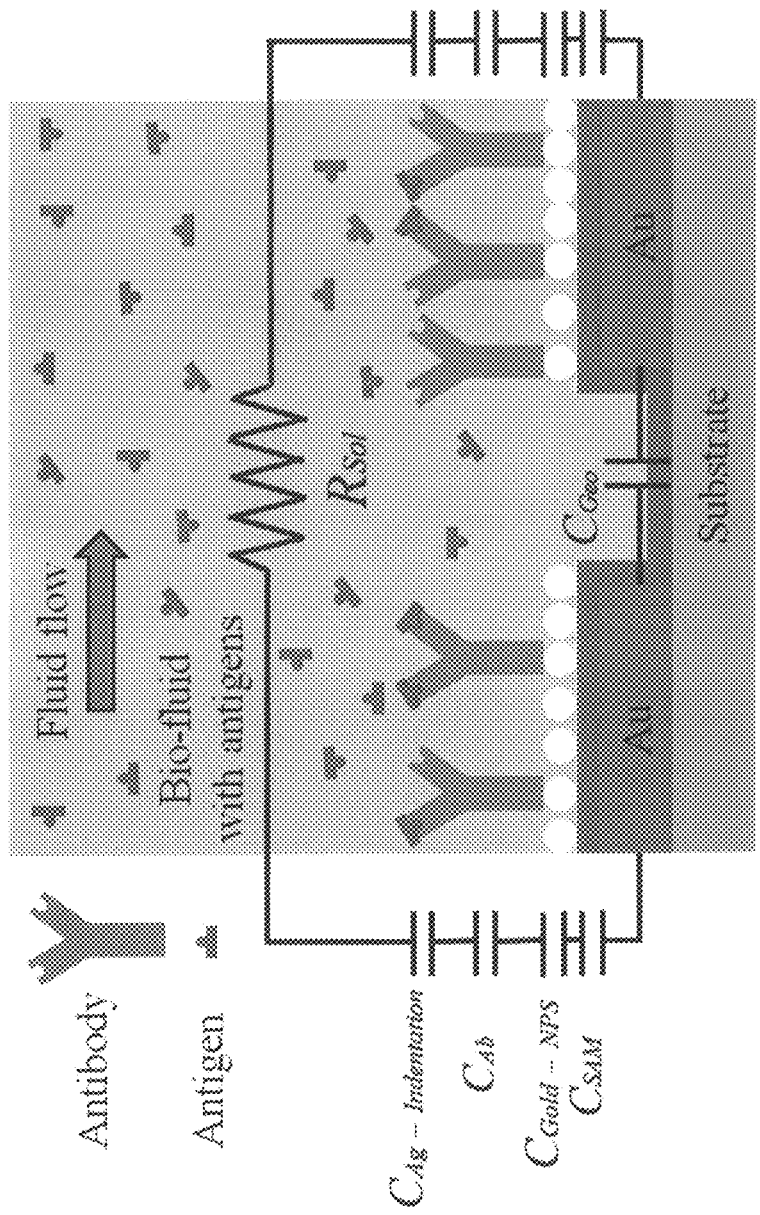
Figure 38:
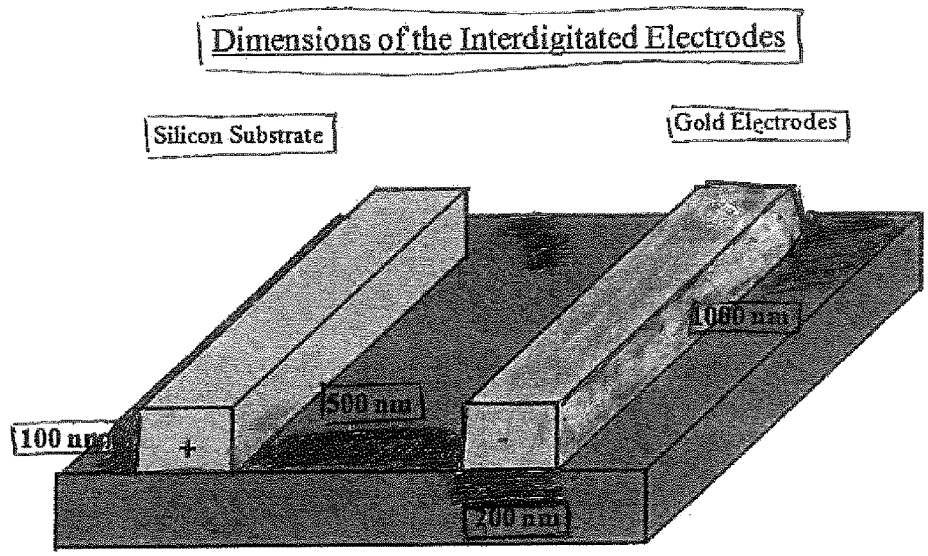
FIG. 38 is a schematic model of a micro biochip packed with all the segments such as PDMS microchannel, disease specific antibodies coating and sensing methodology.
Figure 39:
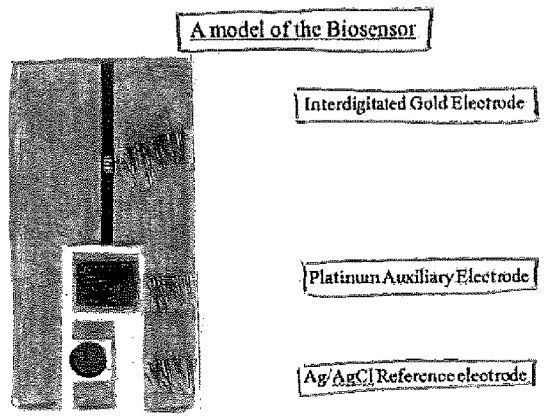
FIG. 39 shows interdigitated electrodes to generate capacitance.
Figure 40:
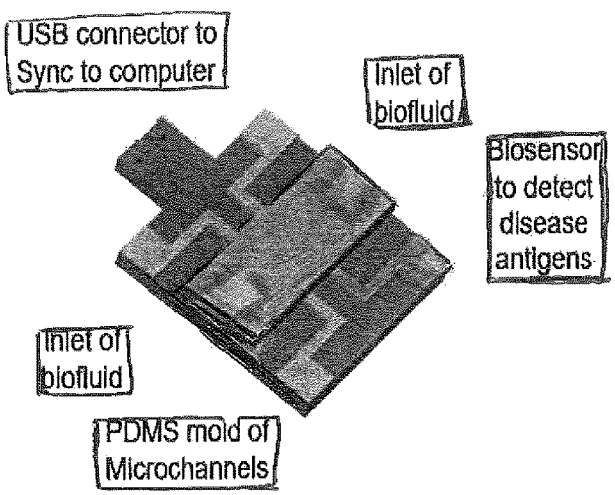
FIG. 40 shows interdigitated electrodes with dimensions shown.
Figure 41:
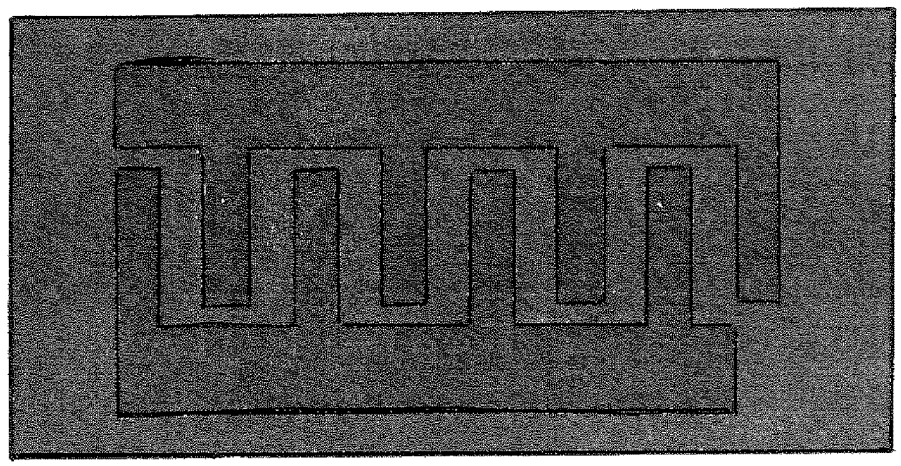
FIG. 41 shows a model of biosensor with interdigitated electrodes.
Figure 42:
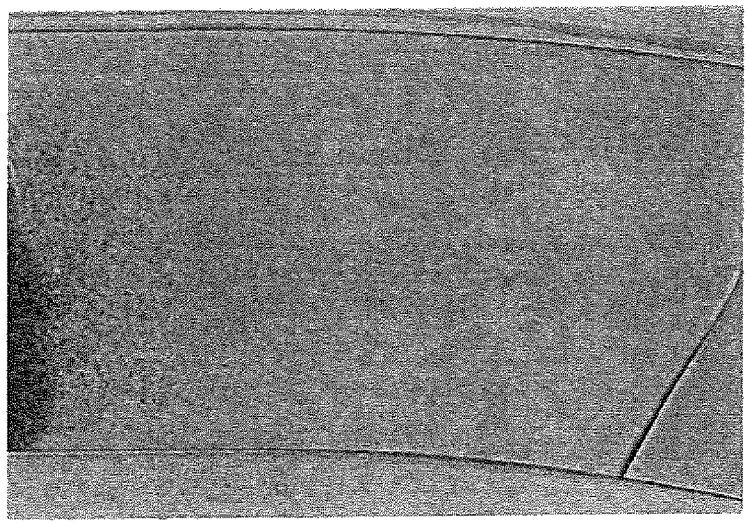
FIG. 42 shows an image of the separated serum flowing in the microchannel when the RBCs stop flowing.
Figure 43:
FIG. 43 illustrates an image of the RBCs forming as lumps in the microchannel where the serum continues to flow in the microchannel.
Figure 44:
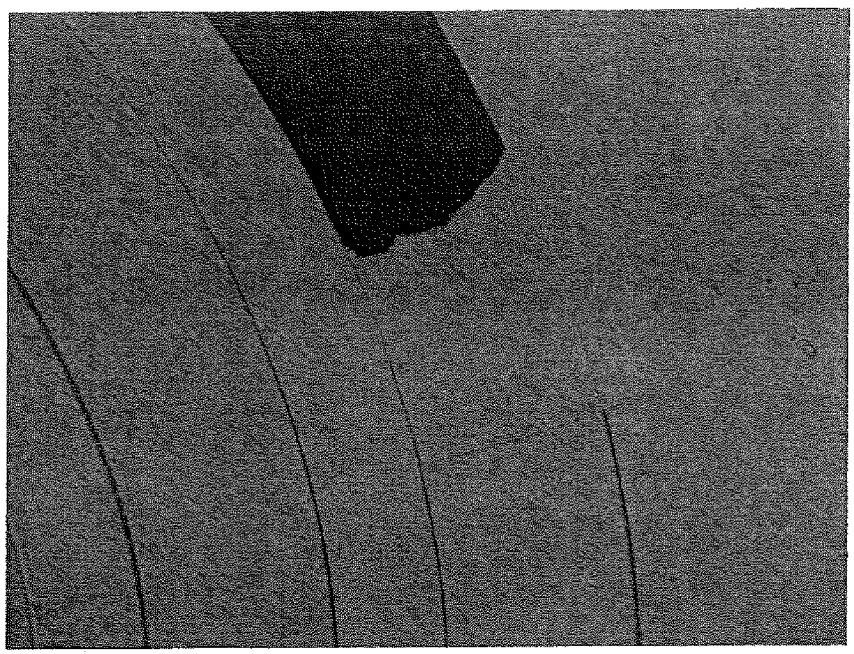
FIG. 44 shows an image of the self-separated serum from whole blood when the blood is flowing by itself (capillary flow) in the microchannel.

Currently, surface imprinted MIPs suffer from blockage and contamination from other proteins within the blood serum. A linear increase of binding sites improves the selectivity at the cost of increased interference from other non-binding proteins. In addition to this draw back, free radical polymerization continues long after UV curing causing a gelation layer on the surface of the MIP. This gelation may interfere with the functional groups causing decreased cavity affinity over time. Indeed, Mattiasson et al. (2016) stated that stable affinity binders are to be used as much as possible; such as surface imprinted MIPs. However, Mattiasson et al. warns that the affinity sites offered by surface MIPs alone are not enough to provide a sufficient solution for bio detection. A potential improvement is to utilize epitope mediated MIPs (FIG. 30) where by having short surface exposed peptides that are used as templates to bind to the entire protein within the analyte. Both selection of a suitable epitope and proper choice of the functional monomer are equally important for successful protein imprinting [30]. Indeed, in 2005 Tai et al. utilized an epitope mediated MIP coated with NS1 viral protein to detect the presence of the Dengue virus within a target analyte[24]. Iskierko and his collaborators stated that epitope imprinting appears promising compared to surface imprinting of whole protein molecules because the structural conformation of molecules exhibited by the small peptides in organic solvents are more easily maintained than that of molecules of entire big proteins [30]. Because surface imprinted and epitope mediated MIPs can suffer from the same drawbacks such as hindrance of its diffusion to a molecular cavity deeply buried inside the MIP, a few studies combined the advantages of surface imprinted and epitope mediated MIPs[30].

In 2006, a hybrid was introduced by Nishino et al. The hybrid model was improved in 2012 when Dechtrirat et al. was able to prepare a novel strategy, which produced a hybrid surface/epitope MIP on a gold-based transducer surface utilizing a synthetic peptide as an imprinting template. The recognition capabilities of this hybrid MIP were impressive as it was able to discriminate between single amino acid mutants and the target peptide [43].

Figure 5:
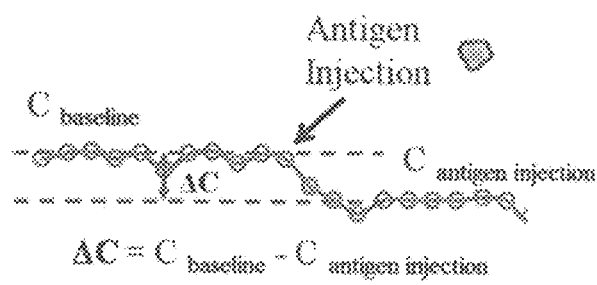
FIG. 5 shows the change in capacitance is measured when the antigen is injected into the system.
Figure 6:
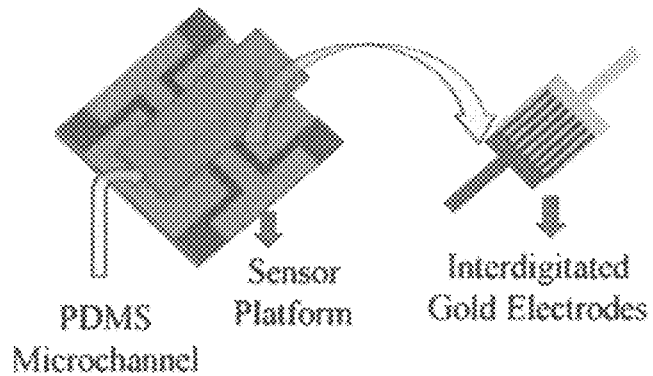
FIG. 6 is a schematic block diagram on the biosensor model of capacitive biosensor with natural antibodies.
Figure 7:
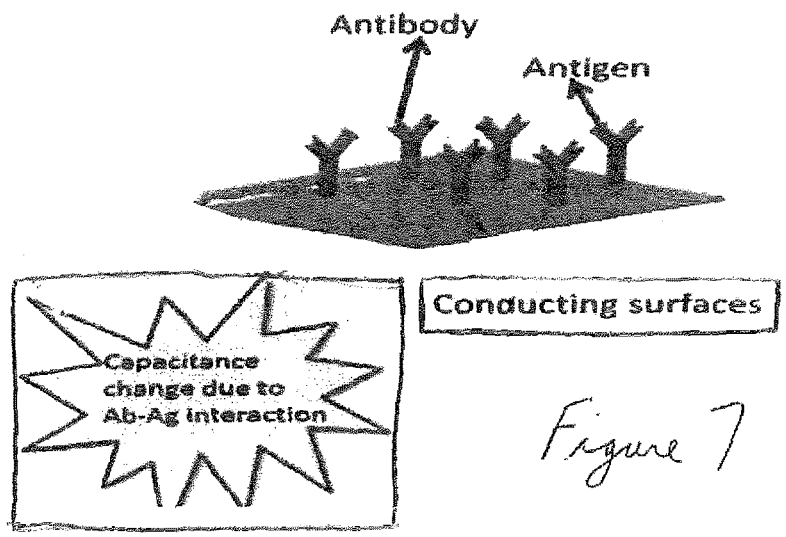
FIG. 7 is a schematic representation of change in the capacitance due to antibodies and antigen interaction.
Figure 8:
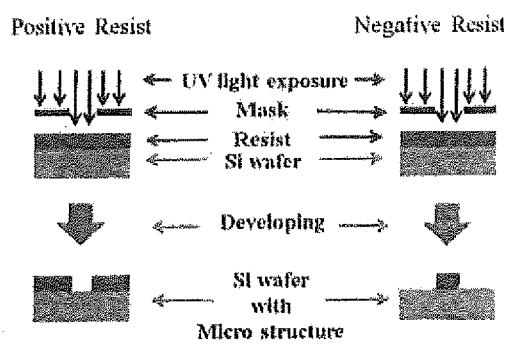
FIG. 8 is a schematic representation of photolithography process for both positive and negative resist on Si wafer.
Figure 9:
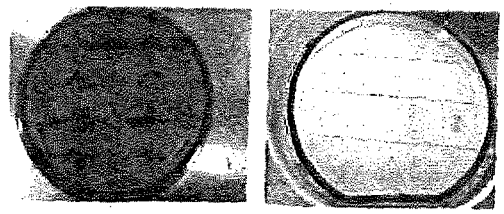
FIG. 9 shows Si wafer after the photolithography process (channels formed from photo resist)—Left & Si wafer after the dry etching process with micro channels of height 107 um—Right.
Figure 10:
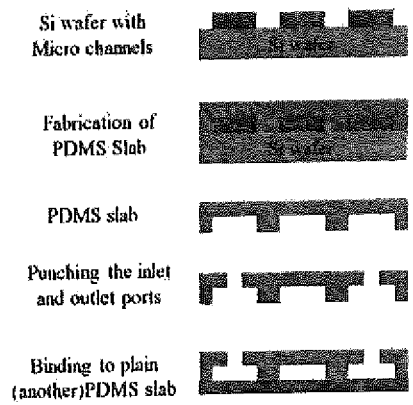
FIG. 10 is a schematic view of the PDMS molds fabrication process using Si wafer with micro channel structures.
Figure 11:
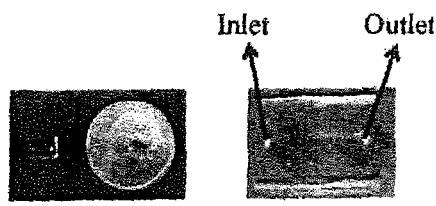
FIG. 11 shows micro biochip size comparison with US quarter coin (Left) & microchannel in the biochip fabricated using photo-lithographic techniques (Right)

In the context of this biosensor, utilization of Galectin-1, which shows high affinity and selectivity to CA-125. To date, no experiments within the literature utilize Galectin-1 as an imprinting protein selective to CA-125 in an MIP application. The advantage here is that biosensor development utilizing Galectin-1 is applicable to both epitope mediated and surface imprinted MIPs. Second, the gelation drawback surface imprinting methods are addressed due to free-radical remnants of the polymerization initiator in the solution. A potential improvement aims to utilize an initiator-transfer-agent-terminator, which binds with the polymerization free radical, turning the growing gelation radical into a dormant species. This method is different from traditional surface contact methods and will be explored experimentally. Finally, create hybrid model of the Mattiasson, Dechtrirat and Ertürk methods. This model introduces a synthetic molecule to specifically bind with CA-125 and leveraging the surface imprinted Galectin-1 cavity as a physical inhibitor to block other potential molecules from affecting the capacitance of the system. In this method, both the epitope and surface imprinted method are leveraged and; unlike the other methods, there are no biological components on the sensing mechanism. Qualitative performance of the gelation control method, along with fabrication improvements, will be determined by fundamental measurement methods such as cyclic voltammetry (CV), differential pulse voltammetry (DPV), electrochemical impedance spectroscopy (EIS), in addition to percentage of protein uptake, selectivity, separation factors, capacity factor k', and chromatographic resolution Rs. In addition, nanoscale detection (ng mL$^{-1}$) will be carried out by cyclic voltammetry utilizing four-electrodes. The results are expected to follow the same shape as the time vs. capacitance diagram in FIG. 5, reproduced from Teeparuksapun et al. (2010) [26]. Fundamental understanding MIP functional selectivity, molecular polymer behavior and engineered tune ability of MIP-antigen interactions are the future outcomes of this research.

Molecular Imprinted Polymers (MIPs) for Biomarker Detection in Micro and Nano Biochip The MIPs can be used as the artificial antibodies in the diagnosis process of the complex diseases like cancer. The MIPs can be fabricated with the desired sensitivity and specificity for individual disease diagnosis process. The MIPs are connected to the electrodes and the interaction of the biomarker with the MIPs can be detected using the electrical signal output.

The MIPs can also be fabricated to diseases not only restricted to cancer. The increased specificity and sensitivity of the MIPs can decrease the false negative and false positive scenarios in the diagnosis process. The MIPs can be sub layered with other bio molecules in order to expand the domain of diagnosis process to other diseases. The MIPs can be used in not only in the electrical sensing systems like identifying the variation in the electrical features but also in the optical sensing systems.

Molecular Imprinted Polymers (MIPs) for Biomarker Detection in Micro and Nano Biochip The MIPs can be used as the artificial antibodies in the diagnosis process of the complex diseases like cancer. The MIPs can be fabricated with the desired sensitivity and specificity for individual disease diagnosis process. The MIPs are connected to the electrodes and the interaction of the biomarker with the MIPs can be detected using the electrical signal output.

The MIPs can also be fabricated to diseases not only restricted to cancer. The increased specificity and sensitivity of the MIPs can decrease the false negative and false positive scenarios in the diagnosis process. The MIPs can be sub layered with other bio molecules in order to expand the domain of diagnosis process to other diseases. The MIPs can be used in not only in the electrical sensing systems like identifying the variation in the electrical features but also in the optical sensing systems.

A micro-contact imprinted surface coating technique is developed here capable of working alongside a capacitive biosensor for highly specific and selective antigen detection. Here, the creation of recognition cavities is utilized.

Materials List
1. 1 M NaOH
2. Ethanol
3. Acetone
4. Phosphate Buffer Solution
5. CA-125 cat. no. A97180H Meridian Life Science, Inc.
6. 99% Pure Tyramine
7. Acryloyl chloride
8. 1-dodecanethiol
9. 50% (w/v) Glutaraldehyde
10. Triethyl-amine
11. Toluene
12. 3-amino-propyl-triethoxysilane (APTES)
13. α,α'-azoisobutyronitrile (AIBN)
14. Methacrylic acid (MMA)
15. Ethylene glycol dimetracrylate (EMMA)
16. 24×40 mm glass microscope cover slips
17. Millipore Milli-Q system capable of reverse osmosis (water source
18. Millipore filter (pore size 0.22 μm)

Procedure

Preparation of the Glass Slides

The 24×40 mm glass cover slips were prepared by cleaning with:
1. 10 mL of 1 M HCL for 10 minutes
   Clean with de-ionized water
2. 10 mL of 1 M NaOH for 10 minutes
   Clean with de-ionized water
3. 10 mL of Ethanol for 10 minutes
   Clean with de-ionized water
4. Dry with Nitrogen gas gun/nozzle.

Preparation of the MIP Stamp

The 24×40 mm glass cover slips are now being prepared to accept the organic components to create the stamp.
1. Prepare a solution of 10% (V/V) APTES (3-amino-propyl-triethoxysilane) (solute) and Ethanol (solvent)
2. Immerse the clean slides in the 10% APTES solution for 1 hour at room temperature.
   This step introduce amino groups onto the surface of the slide.
3. Rinse the surface with Ethanol
4. Prepare a solution of 5% (WV) Glutaraldehyde (GA) in 10 mM phosphate buffer at pH: 7.4
   Glutaraldehyde is a common biological fixative. You can use it to reduce cellular degradation in cells and tissues and entire organisms before you shove it in an SEM. In this application, we are using it as a crosslinker (creating covalent chemical bonds between proteins). You could also use PFA.
   GA is more potent than PEA.
   GA is TOXIC, handle it in the chemical fume hood. Do not dispose of it in the sink. Collect it or inactivate it with milk powder.
5. Immerse the slides into the GA solution for 2 hours at room temperature.
   This step activates the introduced amino groups for the target antibody by leaving a free aldehyde group.

6. Rinse with phosphate buffer and dry with Nitrogen gas
7. Prepare a solution of 0.1 mg/mL CA-125 in 10 mM of phosphate buffer at pH: 7.4
8. Immerse the glass slides in the CA-125 solution for 24 hours at 4 C.

Preparation of the Electrodes
1. Look at the other page for fabrication
2. Immerse the electrodes with ethanol for 10 minutes. Clean with de-ionized water
3. Immerse the electrodes with acetone for 10 minutes. Clean with de-ionized water
4. Prepare an acidic Piranha solution with 3 parts H2SO4 and 1 part. H2O2 (V/V)
   WARNING: Piranha solution is extremely energetic and potentially explosive. Solution is unstable, do not store, do not taste, DO NOT INTRODUCE TO ANY ORGANICS (including waste containers).
5. Immerse the electrodes into the Piranha for 10 minutes. Clean with de-ionized water
6. Load the electrodes into a plasma cleaner for 30 minutes (BNL has a good one).

Electropolymerization of Tyramine
This method introduces free primary amino groups to the surface of electrodes.
1. Prepare an ethanolic solution of 10 mM tyramine
2. Setup the cyclic voltametry machine with the following parameters:
   Set potential range: 0-1.5 V (vs Ag/AgCl)
   Scan rate of 50 mV/s for 15 scans
3. Prepare a solution containing 30 mM Acryloyl chloride and 30 mM triethyl-amine in toluene.
4. Immerse the electropolymerized electrodes into the Acryloyl solution overnight, at room temperature.
   This step generates the amide groups that interact with the protein stamp onto the top surface of the modified electrode.

Polymer Preparation
The proportion of the cross linker must be 4-8 times greater than the monomer. This ensures that the cross linked polymer has an almost negligible solubility. That ratio must be maintained or else you are going to have swelling issues with the MIP. The solvent here maintains the stability of the initiator and monomer radicals thereby allowing the cross-linking and polymerization to achieve a higher molecular weight. The higher the molecular weight, the more rigid the polymer and the less susceptibility to swelling.
1. Prepare a monomer solution 1 part MAA (functional monomer) and 5 parts EGDMA (crosslinker) (V/V) along with AIBN as the initiator.
   Potentially introduce a crosslinking inhibitor here to prevent surface gelation.
2. Pipette 1.5 µL of the monomer solution onto the electrode surface.
3. Bring a protein stamp (glass cover slip) into contact with the electrode surface and hold in place with a paper-clip.
   Ensure the paper clip is not placed on top airy components stamp, electrode or monomer solution. Just clip it in an unused area.
4. Initialize polymerization under UV light at 365 nm @ 400 W for 15 minutes safety goggles).
5. Prepare a solution of 10 mM 1-dodecanethiol in ethanol
6. Remove the protein stamp from the electrode surface.
7. Immerse the electrodes in the 1-dodecanethiol solution for 20 minutes.
   This step ensures there are no pin sized holes in the polymer layer coating the electrode surface.

Procedure for Fabricating Interdigitated Gold Electrodes
1. The Silicon wafer is cut as per the dimensions desired.
2. The Silicon wafer is then Spin coated with positive tone photoresist.
3. The photoresist is PMMA A6. Our desired thickness of electrodes is 100 nm. Ideally the height of the PMMA deposits should me more than 3 times the height of the electrodes.
4. Soft baking of the Silicon wafer is done on hot plate around 180 C for around 90 s.
5. The coated Silicon wafer is then undergone with the Electron beam Lithography procedure as per the CAD model fed on EBL machine.
6. The desired pattern (Interdigitated) is formed over on top of the coated Silicon wafer.
7. The patterned Si wafer is then developed with MIBK: IPA for 60 s and washed with IPA for another 60 s and then dried with nitrogen gas.
8. The patterned Silicon wafer is then placed in Physical vapor deposition machine for deposition of metal on the chip.
9. A layer of Titanium (approx. 10 nm) is deposited on the patterned grooves on the chip. This is done as Titanium improves the adhesion of gold on Silicon.
10. Gold is considered as the metal which is deposited over the chip by high vacuum evaporator (Kurt J Lesker PVD-75 Evaporator).
11. Near about 90 nm of Gold is deposited on top of Si wafer.
12. The lift-off process is performed by removing the positive tone photo resist by cleaning the chip in Acetone Ultrasonic bath for 3 mins and then thoroughly rinsing with Isopropenol in order to prevent redeposition.
13. The fabricated chip is then immersed in diluted Piranha solution for 5 mins and then rinsed with Distilled water and dried with Nitrogen gas.
14. The interdigitated Gold electrode chip is ready to use for addition of other chemicals.

Addition of SAM Layer
One Way
1. The Interdigitated Nano Gold electrodes sensor is then coated with Thiourea which is the SAM layer.
2. A solution of Thiourea is prepared having 10 mM concentration in Millipore-Q water solution.
3. The sensor is then coated with SAM by immersing it into the solution of Thiourea for 12 hours.
4. The surface of the sensor is then rinsed with Ethanol and dH$_2$O and dried using Nitrogen gas.
5. Then the sensor surface is activated by addition using the 50 mM 1-ethyl-3-(-3-dimethylaminopropyl) carbodiimide (EDC) and N-hydroxysuccinimide (NHS) incubated for 4 hrs.
6. The sensor surface is rinsed with double distilled water and Phosphate buffer Solution (PBS).

Alternate Way
7. The sensor is then coated with SAM by immersing it into the solution of 10 mM 3-mercaptopropionic acid (MPA) in absolute ethanol for 24 hours in room temperature.
8. The surface of the sensor is then rinsed with Ethanol and dH$_2$O and dried using Nitrogen gas.
9. Then the sensor surface is activated by addition using the 50 mM 1-ethyl-3-(-3-dimethylaminopropyl) carbodiimide (EDC) and N-hydroxysuccinimide (NHS) incubated for 4 hrs.

10. The sensor surface is rinsed with double distilled water and Phosphate buffer Solution (PBS).
11. The impedimetric or the capacitive changes are measured once the SAM layer is formed.
    NOTE—The formation of the SAM layer is checked through FT-IR.

Addition of Gold Nanospheres on the Nanosensor

12. The PEG encapsulated Gold nanospheres are diluted in Millipore-Q water to the concentration of 30 μg/ml.
13. The Nanosensor is then immersed in this solution for about 8-10 hours.
14. The surface of the Nanosensor is then activated using 50 mM 1-ethyl-3-(-3-dimethylaminopropyl) carbodiimide (EDC) and N-hydroxysuccinimide (NHS) incubated for 3 hrs.
15. The sensor surface is washed with PBS and $dH_2O$.
16. The impedemetric or capacitive response is measured and the Nanosensor is ready to be used for Antibodies Immobilization.

NOTE—The proper Antibodies have to be decided and based on that, it has to be diluted as per the Immunoassay requirements. After that addition of Ethanolamine and BSA addition takes place to increase the Specificity.

Various Layers and how it Works

Gold Electrodes

The gold electrodes are in nanoscale measurements. It has been proven that the nanoscaled size provides better sensitivity compared to conventional electrodes as the electric field generated by the nanoscaled electrodes ranges from 100-200 nm which matches the region of interest since Antigens and Antibodies lies in this range and its effective. [1] The space confinement between the nanoscaled reduces the noises.[2]

SAM Layer:

Generally insulation on top of the gold interdigitated electrodes is a major challenge. [3] Improper insulation may lead to short circuit and increase the level of noise. This may lead to weak signal response. [3][4]

SAM overcomes these challenges and helps in proper insulation. Not only that, SAM layer forms a better adhesion on top of Gold compared to other any oxides or semiconductors.[3][4] In our experiment we are using layer of Thiourea which gives good insulation and better results.

Gold Nanoparticles

The gold nanoparticles are the substances that are playing the most crucial role in increasing our sensitivity in our experiment. The modified gold nanoparticles not only provide stability for immobilization but also help in increasing the number of antibodies on top of it [5]. Gold nanoparticles have high surface to volume ratio, surface energy and their ability to decrease the distance between proteins and metal particles. These properties help in binding ultra low target concentration within a specific constant area. The increase in number of concentration of antibodies is because of their free orientation on the surface of the gold nanoparticles.[5][6] This increases the density in same amount of area. In general the attachments of the gold nanoparticles with antibodies are through ionic interaction. [5] This is because the gold nanoparticles are negatively charged and the Antibodies are positively.

In experiments, PEG encapsulated gold nanoparticles were provided whose surfaces are to be activated using EDC and NHS. Then the antibodies are binded to the nanoparticles through covalent bonds. So better adhesion and immobilization of Antibodies on top of Gold nanoparticles is achieved as the binding is not only because of ionic interaction but also because of covalent bonding. [5] This increases the stability of the surface for the antibody immobilization that retains their biological activities. So it will be more effective in sensing and immobilization even when micro fluid is passing through on top of them compared to traditional gold nanoparticles.

Antibodies

The desired antibodies are diluted to the required concentration and then prepared in a buffer solution. Then the modified Nanobiosensor is immersed in the Antibodies solution. The electrical measurements are done before the antibodies immobilization and then again after the immobilization. The confirmation of antibodies is further verified by FT-IR or SEM.

In later part BSA modified Antibodies are used as the BSA helps in increasing the specificity. The alternate process can also be achieved by addition of ethanolamine as it blocks all the other non-reactive groups and helps in decreasing the noise. [4]

Antigens

Last but not least turns up the antigens. The antigens are basically present in the blood or the microfluid that passes on top of the nanosensor through microfluidic channel.

Working—Since the capacitance method depends on the dielectric factors, so when the Antigens interacts with the Antibodies these increases the molecular size of the complex that formed. [7] As a result, a local disturbance of the distribution of bound charges will create a dipole moment which will occur in the dielectric interface. [4] Therefore, large permanent dipole moment stimulates dielectric polarization on the sensor surface. All the biological samples have an arrangement of electric charge carriers. These charges are displaced by an external electric field and polarized to neutralize the effect of an external field. With this phenomenon, the dielectric of each analyte over the frequency spectrum has its unique characteristics which we measure and see the change. [4] As a result, the measured capacitance or impedance of the sensor varies with the relative change in dielectric properties of modified sensor surface.

Biomarker Detection Using the Interdigitated Electrodes in the Microchannel of the Biochip The disease biomarker can be diagnosed using the nanocircuit in the microfluidic environment. The interdigitated electrodes can be of different conducting materials. The coating of AG/AB can be of various diseases, such as cancer. The electrode dimensions are variable with respect to the capacitance generation. The intermediate layers between the electrodes and the AG/AB are fabricated using the coating on the electrodes with different materials like GOLD nano particles to enhance the sensing ability.

The intermediate layers can also include biomaterials along with the conducting materials like Bovine Serum Albumin (BSA) in order to increase the AG/AB interaction. The interdigitated electrodes are implemented in the microfluidic environment and specified shaped micro channels. The interdigitated electrodes is used to measure the capacitance change when the AG/AB interaction with biomarkers but the electrodes can also be used for other electrical measurements and variations.

Self-Separation of Serum During the Capillary Flow of Blood Through Microchannel The blood can be separated by itself using the design of the microchannel. The blood flows in the micro channel with no external pressure. The flow of blood in micro channel is because of the capillary effect. The capillary flow of blood in the curved section of the micro channel experience forces like centrifugal force which separates the liquid from the solid matters in the blood. The various densities of the different segments in blood experience the different centrifugal effects while flowing through the curved section of the microchannel, which separates the serum from the blood.

The serum can be separated from various solid matter like RBCs, WBCs and platelets of blood without using any external devices. The separation is instantly started soon after the blood flow in the microchannel. Self-separation of the serum in the micro channel can be implemented in various diagnosis process and significantly reduce the man power and efforts in the diagnosis process. The separation can be done when the blood flow in the microchannel, there will not be any need to external equipment to handle blood which may limit the contamination. The separation of the serum from the whole blood does not require any sample preparation process.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

Accordingly, although the invention herein has been described with reference to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

REFERENCES

[1] Nunna, B. B., Zhuang, S., Malave, I., Lee, E. S. (2015). Ovarian Cancer Diagnosis using Micro Biochip, NIH-IEEE 2015 Strategic Conference on Healthcare Innovations and Point-of-Care Technologies for Precision Medicine, (PCHT15-0056) Nov. 9-10, 2015, Bethesda, Md.

[2] American Cancer Society. Cancer Facts & FIGS. 2016. Atlanta: American Cancer Society; Page 4.

[3] Lucas, Richard. "Ueber das Zeitgesetz des kapillaren Aufstiegs von Flüssigkeiten." Colloid & Polymer Science 23, no. 1 (1918): 15-22.

[4] Washburn, Edward W. "The dynamics of capillary flow." Physical review 17, no. 3 (1921): 273.

[5] Dou, Yue-Hua, Ning Bao, Jing-Juan Xu, and Hong-Yuan Chen. "A dynamically modified microfluidic poly (dimethylsiloxane) chip with electrochemical detection for biological analysis." Electrophoresis 23, no. 20 (2002): 3558-3566.

[6] Alcantar, Norma A., Eray S. Aydil, and Jacob N. Israelachvili. "Polyethylene glycol-coated biocompatible surfaces." Journal of biomedical materials research 51, no. 3 (2000): 343-351.

[7] Eddington, David T., John P. Puccinelli, and David J. Beebe. "Thermal aging and reduced hydrophobic recovery of polydimethylsiloxane." Sensors and Actuators B: Chemical 114, no. 1 (2006): 170-172.

[8] Ginn, Brent T., and Oliver Steinbock. "Polymer surface modification using microwave-oven-generated plasma." Langmuir 19, no. 19 (2003): 8117-8118.

[9] Xiao, Deqing, Hui Zhang, and Mary Wirth. "Chemical modification of the surface of poly (dimethylsiloxane) by atom-transfer radical polymerization of acrylamide." Langmuir 18, no. 25 (2002): 9971-9976.

[10] Tan, S. H., Nguyen, N. T., Chua, Y. C., & Kang, T. G. (2010). Oxygen plasma treatment for reducing hydrophobicity of a sealed polydimethylsiloxane micro channel. Bio microfluidics, 4(3), 032204.

[11] Hrncir, E., and J. Rosina. "Surface tension of blood." Physiological research/Academia Scientiarum Bohemoslovaca 46.4 (1996): 319-321.

[12] Nunna, B., Lee, E. S., (2015). Hemorheology characteristics in PDMS micro channel with varied surface treatments, (InterPACKICNMM2015-48510). ASME 13th Int'l Conference on Nano-channels, Microchannels and Minichannels (ICNMM). (Jul. 6-9, 2015), San Francisco, Calif.

[13] Nunna, B. B., Zhuang, S., Lee, E. S. (2015). Hemorheology In PDMS Micro Channel With Varied Surface Roughness (KP1.00116)—68th Annual Meeting of the American Physical Society—Division of Fluid Dynamics Meeting, 2015, Nov. 22-24, 2015, Boston, Mass.

[14] Nunna, B B., S Zhuang., Lee, E. S., (2016). Influence on capillary flow of human blood in PDMS micro channels due to various surface treatments, (ICNMM2016-8122). ASME 2016, 14th International Conference on Nanochannels, Microchannels and Minichannels (ICNMM), (Jul. 10-14, 2016), Washington, D.C.

[15] Nunna, B. B., Zhuang, S., Lee, E. S. (2016). Point-of-Care (POC) Micro Biochip for Ovarian Cancer Diagnostics. Journal of Translational Engineering in Health and Medicine. (In Review).

[16] Lee, E. S., Nunna, B. B., Micro Bio-Chip for disease diagnosis with capacitance sensing method, Invention ID: 16-003. NJIT, May 26, 2015 (Filed at NJIT)

[17] Lee, E. S., Nunna, B. B., Micro Bio-Chip for disease diagnosis with temperature and oscillation sensing method, Invention ID: 16-002. NJIT, May 24, 2015 (Filed at NJIT)

[18] Lee, E. S., Nunna, B. B., Microfluidic Chip-based Disease Diagnosis Device, Invention ID: 15-024. NJIT, Jan. 22, 2015 (Filed at NJIT)

[19] B. Sellergren, Ed., Molecularly imprinted polymers: man-made mimics of antibodies and their applications in analytical chemistry, 1st ed. Amsterdam; New York: Elsevier, 2001.

[20] L. Chen, S. Xu, and J. Li, "Recent advances in molecular imprinting technology: current status, challenges and highlighted applications," Chem. Soc. Rev., vol. 40, no. 5, pp. 2922-2942, May 2011.

[21] H. Nishino, C.-S. Huang, and K. J. Shea, "Selective Protein Capture by Epitope Imprinting," Angew. Chem. Int. Ed., vol. 45, no. 15, pp. 2392-2396, April 2006.

[22] "Molecularly Imprinted Materials: Science and Technology," CRC Press, 30 Nov. 2004. [Online]. Available: https://www.crcpress.com/Molecularly-Imprinted-Materials-Science-and-Technology/Yan/p/book/9780824753535. [Accessed: 29 Jun. 2016].

[23] J. Wackerlig and R. Schirhagl, "Applications of Molecularly Imprinted Polymer Nanoparticles and Their Advances toward Industrial Use: A Review," Anal. Chem., vol. 88, no. 1, pp. 250-261, January 2016.

[24] J. K. Gohagan, P. C. Prorok, R. B. Hayes, B. S. Kramer, and Prostate, Lung, Colorectal and Ovarian Cancer Screening Trial Project Team, "The Prostate, Lung, Colorectal and Ovarian (PLCO) Cancer Screening Trial of the National Cancer Institute: history, organization, and status," Control. Clin. Trials, vol. 21, no. 6 Suppl, p. 251S-272S, December 2000.

[25] S. Viswanathan, C. Rani, S. Ribeiro, and C. Delerue-Matos, "Molecular imprinted nanoelectrodes for ultra sensitive detection of ovarian cancer marker," Biosens. Bioelectron., vol. 33, no. 1, pp. 179-183, March 2012.

[26] J. Wang and S.-T. Yau, "Field-effect amperometric immuno-detection of protein biomarker," Biosens. Bioelectron., vol. 29, no. 1, pp. 210-214, November 2011.

[27] L. Wu, F. Yan, and H. Ju, "An amperometric immunosensor for separation-free immunoassay of CA125 based on its covalent immobilization coupled with thionine on carbon nanofiber," J. Immunol. Methods, vol. 322, no. 1-2, pp. 12-19, April 2007.

[28] Y. Choi and S.-T. Yau, "Field-effect enzymatic amplifying detector with picomolar detection limit," Anal. Chem., vol. 81, no. 16, pp. 7123-7126, August 2009.

[29] J. E. Dick, A. T. Hilterbrand, L. M. Strawsine, J. W. Upton, and A. J. Bard, "Enzymatically enhanced collisions on ultramicroelectrodes for specific and rapid detection of individual viruses," Proc. Natl. Acad. Sci., vol. 113, no. 23, pp. 6403-6408, June 2016.

[30] Z. Iskierko, P. S. Sharma, K. Bartold, A. Pietrzyk-Le, K. Noworyta, and W. Kutner, "Molecularly imprinted polymers for separating and sensing of macromolecular compounds and microorganisms," Biotechnol. Adv., vol. 34, no. 1, pp. 30-46, January 2016.

[31] G. Ertûrk, M. Hedstrôm, M. A. Tümer, A. Denizli, and B. Mattiasson, "Real-time prostate-specific antigen detection with prostate-specific antigen imprinted capacitive biosensors," Anal. Chim. Acta, vol. 891, pp. 120-129, September 2015.

[32] M. J. Whitcombe, L. Martin, and E. N. Vulfson, "Predicting the selectivity of imprinted polymers," Chromatographia, vol. 47, no. 7-8, pp. 457-464.

[33] J. Li, G. Wei, and Y. Zhang, "Chapter 2—Molecularly Imprinted Polymers as Recognition Elements in Sensors," in Molecularly Imprinted Sensors, Amsterdam: Elsevier, 2012, pp. 35-55.

[34] M. I. Page and W. P. Jencks, "Entropic contributions to rate accelerations in enzymic and intramolecular reactions and the chelate effect," Proc. Natl. Acad. Sci., vol. 68, no. 8, pp. 1678-1683, 1971.

[35] W. P. Jencks, "On the attribution and additivity of binding energies," Proc. Natl. Acad. Sci., vol. 78, no. 7, pp. 4046-4050, July 1981.

[36] D. H. Williams, J. P. Cox, A. J. Doig, M. Gardner, U. Gerhard, P. T. Kaye, A. R. Lal, I. A. Nicholls, C. J. Salter, and R. C. Mitchell, "Toward the semiquantitative estimation of binding constants. Guides for peptide-peptide binding in aqueous solution," J. Am. Chem. Soc., vol. 113, no. 18, pp. 7020-7030, 1991.

[37] I. A. Nicholls, "THERMODYNAMIC CONSIDERATIONS FOR THE DESIGN OF AND LIGAND RECOGNITION BY MOLECULARY IMPRINTED POLYMERS," Chem. Lett., no. 11, pp. 1035-1036, 1995.

[38] J. O. Mahony, K. Nolan, M. R. Smyth, and B. Mizaikoff, "Molecularly imprinted polymers—potential and challenges in analytical chemistry," Anal. Chim. Acta, vol. 534, no. 1, pp. 31-39, April 2005.

[39] N. Perez-Moral and A. Mayes, "Comparative study of imprinted polymer particles prepared by different polymerisation methods," Anal. Chim. Acta, vol. 504, no. 1, pp. 15-21, February 2004.

[40] L. Chen, X. Wang, W. Lu, X. Wu, and J. Li, "Molecular imprinting: perspectives and applications," Chem. Soc. Rev., vol. 45, no. 8, pp. 2137-2211, April 2016.

[41] B. Mattiasson and M. Hedström, "Capacitive biosensors for ultra-sensitive assays," TrAC Trends Anal. Chem., vol. 79, pp. 233-238, May 2016.

[42] D.-F. Tai, C.-Y. Lin, T.-Z. Wu, and L.-K. Chen, "Recognition of dengue virus protein using epitope-mediated molecularly imprinted film," Anal. Chem., vol. 77, no. 16, pp. 5140-5143, August 2005.

[43] D. Dechtrirat, K. J. Jetzschmann, W. F. M. Stöcklein, F. W. Scheller, and N. Gajovic-Eichelmann, "Protein Rebinding to a Surface-Confined Imprint," Adv. Funct. Mater., vol. 22, no. 24, pp. 5231-5237, December 2012.

[44] K. Teeparuksapun, M. Hedström, E. Y. Wong, S. Tang, I. K. Hewlett, and B. Mattiasson, "Ultrasensitive Detection of HIV-1 p24 Antigen Using Nanofunctionalized Surfaces in a Capacitive Immunosensor," Anal. Chem., vol. 82, no. 20, pp. 8406-8411, October 2010.

[45] Altintas, Zeynep, Sreenivasa Saravan Kallempudi, and Yasar Gurbuz. 2014. "Gold Nanoparticle Modified Capacitive Sensor Platform for Multiple Marker Detection." Talanta 118 (January): 270-76. doi:10.1016/j.talanta.2013.10.030.

[46] Cui, Haochen. 2015. "Alternating Current Electrokinetics based capacitive affinity biosensor: A point of care diagnostic platform." http://trace.tennessee.edu/utk_grad-diss/3411/.

[47] Kallempudi, Sreenivasa Saravan, and Yasar Gurbuz. 2011. "A Nanostructured-Nickel Based Interdigitated Capacitive Transducer for Biosensor Applications." Sensors and Actuators B: Chemical 160 (1): 891-98. doi: 10.1016/j.snb.2011.08.078.

[48] Qureshi, Anjum, Javed H. Niazi, Saravan Kallempudi, and Yasar Gurbuz. 2010. "Label-Free Capacitive Biosensor for Sensitive Detection of Multiple Biomarkers Using Gold Interdigitated Capacitor Arrays." Biosensors and Bioelectronics 25 (10): 2318-23. doi:10.1016/j.bios.2010.03.018.

[49] Tsouti, V., C. Boutopoulos, I. Zergioti, and S. Chatzandroulis. 2011. "Capacitive Microsystems for Biological Sensing." Biosensors and Bioelectronics 27 (1): 1-11. doi:10.1016/j.bios.2011.05.047.

[50] Zou, Zhiwei, Junhai Kai, Michael J. Rust, Jungyoup Han, and Chong H. Ahn. 2007. "Functionalized Nano Interdigitated Electrodes Arrays on Polymer with Integrated Microfluidics for Direct Bio-Affinity Sensing Using Impedimetric Measurement." Sensors and Actuators A: Physical 136 (2): 518-26. doi:10.1016/j.sna.2006.12.006.

[51] Hoffmann, B., Gadau, M., Paeschke, M., Hintsche, R., 1995. Proc. (Transducers' 95). Eight Int. Conf. on Solid-State Sensors and Actuators, Sweden, pp. 837-840.

[52] Gul, O., Heves, E., Kaynak, M., Basaga, H., Gurbuz, Y., 2006. Proc. 2006 IEEE International Conference on Sensors, Korea, pp. 600-603.

[53] Gerwen, P. V., Laureyn, W., Laureys, W., Huyberechts, G., Op De Beeck, M., Baert, K., Suls, J., Sansen, W., Jacobs, P., Hermans, L., Mertens, R., 1998. Sens. Actuators B 49, 73-80

[54] Laczka, O., Baldrich, E., Mu~noz, F. X., Del Campo, F. J., 2008. Anal. Chem. 80, 7239-7247.

[55] Laczka, O., Del Campo, F. J., Mu~noz, F. X., 2007. Biosens. Bioelectron. 22, 1205-1217.

[56] Gouy, G., 1910. J. Phys. 9, 457-468.

[57] Qureshi, A., Niazi, J. H., Kallempudi, S., Gurbuz, Y., 2010. Biosens. Bioelectron. 25, 2318-2323.

[58] Thompson, M., Ellison, S. L. R., 2005. Accredit. Qual. Assur. 10, 82-97.

[59] Tosar, J. P., Brañas, G., Laíz, J., 2010. Biosens. Bioelectron. 26, 1205-1217.
[60] Carlen, E. T., Weinberg, M. S., Dubé, C. E., Zapata, A. M., Borenstein, J. T., 2006. Appl. Phys. Lett. 89, 173123.
[61] Carlen, E. T., Weinberg, M. S., Zapata, A. M., Borenstein, J. T., 2008. Rev. Sci. Instrum. 79, 015106
[62] Carrara, S., Bhalla, V., Stagni, C., Benini, L., Ferretti, A., Valle, F., Gallotta, A., Riccò, B., Samorì, B., 2009. Sens. Actuators B 136, 163-172.
[63] Park, K. K., Lee, H. J., Yaralioglu, G. G., Ergun, A. S., Oralkan, Ö., Kupnic, M., Quate, C. F., Khuri-Yakub, B. T., Braun, T., Ramseyer, J.-P., Lang, H. P., Hegner, M., Gerber, Ch., Gimzewski, J. K., 2007. Appl. Phys. Lett. 91, 094102.
[64] X. Zhu, C. H. Ahn, Electrochemical determination of reversible redox species at interdigitated array micro/nanoelectrodes using charge injection method, IEEE Trans. Nanobiosci. 4 (2005) 164-169.
[65] Dreaden E C, Alkilany A M, Huang X, Murphy C J, El-Sayed M A (2012) The golden age: gold nanoparticles for biomedicine. Chem Soc Rev 41: 2740-2779. doi: 10.1039/c1cs15237h PMID: 22109657
[66] Thakor A, Jokerst J, Zavaleta C, Massoud T, Gambhir S (2011) Gold nanoparticles: a revival in precious metal administration to patients. Nano Lett 11: 4029-4036. doi: 10.1021/nl202559p PMID:21846107
[67] V. M. Mirsky, M. Riepl, O. S. Wolfbeis, Capacitive monitorino of protein immobilization and antigen-antibody reactions on monomolecular alkylthiol films on gold electrodes, Biosens. Bioelectron. 12 (1997) 977-989.
[68] P. van Gerwen, W. Laureyn, W. Laureys, G. Huyberechts, M. O. D. Beeck, K. Baert, J. Suls, W. Sansen, P. Jacobs, L. Hermans, R. Mertens, Nanoscaled interdigitated electrodes array for biochemical sensors, Sens. Actuators B 49 (1998) 73-80.
[69] M. Yi, K. H. Jeong, L. P. Lee, Theoretical and experimental study towards a nanogap dielectric biosensor, Biosens. Bioelectron. 20 (2005) 1320-1326.

SECONDARY REFERENCES

[1] Laczka, O., Baldrich, E., Muñoz, F. X. and del Campo, F. J., 2008. Detection of *Escherichia coli* and *Salmonella typhimurium* using interdigitated microelectrode capacitive immunosensors: the importance of transducer geometry. *Analytical chemistry*, 80(19), pp. 7239-7247.
[2] Yi, M., Jeong, K. H. and Lee, L. P., 2005. Theoretical and experimental study towards a nanogap dielectric biosensor. *Biosensors and Bioelectronics*, 20(7), pp. 1320-1326.
[3] Berggren, C., Bjarnason, B. and Johansson, G., 2001. Capacitive biosensors. Electroanalysis, 13(3), pp. 173-180.
[4] Kallempudi, S. S. and Gurbuz, Y., 2011. A nanostructured-nickel based interdigitated capacitive transducer for biosensor applications. *Sensors and Actuators B: Chemical*, 160(1), pp. 891-898.
[5] Jazayeri, Mir Hadi, Hamed Amani, Ali Akbar Pourfatollah, Hamidreza Pazoki-Toroudi, and Bijan Sedighimoghaddam. "Various Methods of Gold Nanoparticles (GNPs) Conjugation to Antibodies." *Sensing and Bio-Sensing Research* 9 (July 2016): 17-22.
[6] Dreaden, E. C., Alkilany, A. M., Huang, X., Murphy, C. J. and El-Sayed, M. A., 2012. The golden age: gold nanoparticles for biomedicine. *Chemical Society Reviews*, 41(7), pp. 2740-2779
[7] Carrara, S., Bhalla, V., Stagni, C., Benini, L., Ferretti, A., Valle, F., Gallotta, A., Riccò, B. and Samorì, B., 2009. Label-free cancer markers detection by capacitance biochip. Sensors and Actuators B: Chemical, 136(1), pp. 163-172.

What is claimed is:

1. A method of using a biomarker detection and serum self-separation device, comprising:
providing a single micro biochip having a molecular imprinted polymer (MIP) that is used as an artificial antibody to sense an antigen/antibody (AG/AB) interaction, wherein the MIP is disposed unto an interdigitated electrode that is part of a nano circuit on the biochip, and the biochip is a self-evaluation device that functions by itself without any aid of external devices;
placing a biofluid sample containing an antigen on the biochip;
detecting the AG/AB interaction of a biomarker with the MIP using an electrical signal output with a hybrid method utilizing at least a variation of capacitance charge;
diagnosing a disease in the biofluid sample; and
determining a severity of the disease is sensed depending on intensity of the signal output.

2. The method of claim 1, wherein the electrode contains gold (Au).

3. The method of claim 1, wherein the electrical signal is a change in capacitance in the nano circuit.

4. The method of claim 1, wherein the diagnosing is for a complex disease including cancer.

5. The method of claim 1, wherein the MIP is fabricated with a desired sensitivity and specificity for a specific disease.

6. The method of claim 5, wherein the sensitivity and specificity of the MIP decreases false negative and false positive diagnosis scenarios.

7. The method of claim 1, wherein the MIP is sub-layered with various biomolecules in order to diagnosis various diseases.

8. The method of claim 1, wherein the interdigitated electrode is placed in a specific shaped microchannel of the biochip.

9. The method of claim 1, further including diagnosing a disease biomarker using the nanocircuit in a microfluidic environment.

10. The method of claim 1, wherein the interdigitated electrode has a plurality of fingers that are patterned and made of different conducting materials.

11. The method of claim 1, wherein the interdigitated electrodes dimensions are directly related to capacitance generation.

12. The method of claim 1, wherein the interdigitated electrodes further includes intermediate layers between the electrodes and an AG/AB complex formed by the AG/AB interaction of the antigen and the artificial antibody, and the intermediate layers are a coating to enhance the sensing ability.

13. The method of claim 12, wherein the intermediate layers are selected from a group consisting of a conductive metal, gold (AU) nano particles, bovine serum albumin (BSA), a biomaterial, and any combination thereof.

14. The method of claim 1, wherein the hybrid method further includes Temperature Variation, and Variation Electric Oscillation to detect and diagnose both the disease and the severity of the disease.

15. The method of claim 1, wherein the biofluid sample is directly applied on the biochip without any sample preparation requirement, and the nano circuit generates necessary forces and electrical charges required for the functionality of the biochip without any aid of external devices.

16. The method of claim 1, wherein the biofluid is separated in a microchannel of the biochip without bifurcating the microchannel so that the biofluid is separated into liquid and solid matters with use of only the microchannel.

17. The method of claim 1, wherein the biochip further includes a microchannel having a natural antibody, and the antigen from the biofluid forms an antigen-antibody (AG/AB) complex.

18. The method of claim 17, further includes a sensor mechanism on the biochip to detect the AG/AB interaction from both the natural antibody and the artificial antibody of the MIP.

* * * * *